United States Patent [19]
Uhl et al.

[11] Patent Number: 5,312,734
[45] Date of Patent: May 17, 1994

[54] CDNA ENCODING A DOPAMINE TRANSPORTER

[75] Inventors: George R. Uhl, Towson; Michael J. Kuhar, Baltimore; Shoichi Shimada, Baltimore; Shigeo Kitayama, Baltimore; Amrat Patel, Baltimore; Chien-Liang Lin, Baltimore, all of Md.

[73] Assignee: The United States of America as represented by the Department of Health and Human Services, Washington, D.C.

[21] Appl. No.: 762,132

[22] Filed: Sep. 20, 1991

[51] Int. Cl.5 .................. C12P 21/06; C12N 5/00; C12N 15/00; C07H 15/12
[52] U.S. Cl. .................. 435/69.1; 435/2; 435/4; 435/6; 435/30; 435/41; 435/240.2; 435/320.1; 530/350; 530/387.9; 530/395; 530/388.22; 530/389.1; 536/23.1; 536/23.4; 536/23.5
[58] Field of Search .................. 435/69.1, 2, 4, 6, 41, 435/240.2, 320.1, 30; 530/350, 387, 395; 536/27, 23.1, 23.4, 23.5

[56] References Cited

PUBLICATIONS

Science (1987) Ritz et al. vol. 237, pp. 1219–1223.
Shimada et al. (S. Shimada et al, Science 254:576 (1991)).
Kilty et al (J. E. Kilty et al, Science 254:578 (1991).
Pacholczyk et al. (T. Pachlczyk et al, Nature 350:350(1991)).
Gaustella et al (J. Guastella et al, Science 249:1303 (1990)).
Uhl et al. (G. R. Uhl et al, Mol. Brain Res. 9:23 (1991)).
Bannon et al. (M. J. Bannon et al, J. Neurochemistry 54:706 (1990)).
Anderson et al, (M. P. Anderson et al, Science 253:202 (1991)).
Sallee et al (F. R. Sallee et al, FEBS Letters 256: 219 (1989).
Berger et al (S. P. Berger et al., Mol. Pharmacol. 39:429 (1991)).
Grigoriadis et al. (D. E. Gigoriadis et al, J. Neuroscience 9:2664 (1989)).
Niznik et al. (H. B. Niznik et al., Arch. Biochem. Biophys. 276:424 (1990)).
Krueger (B. K. Krueger, J. Neurochemistry 55:260 (1990)).

Primary Examiner—Robert J. Hill, Jr.
Assistant Examiner—Alan P. Wang
Attorney, Agent, or Firm—Birch, Stewart, Kolasch & Birch

[57] ABSTRACT

The invention described in this disclosure relates to a cloned cDNA encoding the dopamine transporter protein usually found in certain neural cells. The invention is further directed to the purified dopamine transporter protein and its use as a biosensor material and immunogen for the production of anti-DAT1 antibodies. The disclosure also discusses methods for use of the cDNA for diagnostic and treatment applications, and methods for use of permanent cell lines transformed with the dopamine transporter cDNA for pharmaceutical screening. The use of anti-DAT1 antibodies as a diagnostic tool is also addressed.

8 Claims, 15 Drawing Sheets pDAT sequence:

```
5'    1 GAATTCCCGC AGGAGTCAGT CGAAGAAGAA AGAAGCAGAG TTCCTTGGGC
     51 TCCGGTCTAC CCATGAGTAA GAGCAAATGC TCCGTGGGAC CAATGTCTTC
    101 AGTGGTGGCC CCGGCTAAAG AGTCCAATGC TGTGGGCCCC AGAGAGGTGG
    151 AGCTCATCCT GGTCAAGGAG CAGAACGGAG TGCAGCTGAC CAACTCCACC
    201 CTCATCAACC CGCCACAGAC ACCAGTGGAG GCTCAAGAGC GGGAGACCTG
    251 GAGCAAGAAA ATTGATTTCC TGCTATCAGT CATCGGCTTT GCTGTGGACC
    301 TGGCCAATGT CTGGAGGTTT CCCTACCTGT GCTACAAAAA TGGTGGAGGT
    351 GCCTTCCTGG TGCCCTACCT GCTCTTCATG GTTATTGCTG GGATGCCCCT
    401 CTTCTACATG GAGCTGGCTC TCGGACAGTT CAACAGAGAA GGAGCTGGTG
    451 GTGTCTGGAA GATCTGTCCT GTCCTGAAAG GTGTGGGCTT CACTGTTATC
    501 CTCATCTCTT CTACGTGGG CTTCTTCTAC AATGTCATCA TCGCATGGGC
    551 ACTGCACTAC TTCTTCTCCT CCTTCACCAT GGACCTCCCA TGGATCCACT
    601 GCAACAACAC CTGGAATAGC CCCAACTGCT CCGATGCCCA TGCCAGCAAC
    651 TCTAGCGACG GCCTGGGCCT CAATGACACC TTTGGGACCA CACCCGCTGC
    701 TGAGTACTTT GAGCGTGGCG TGCTGCACCT TCACCAGAGC CGTGGCATTG
    751 ATGACCTGGG CCCTCCACGG TGGCAGCTCA CAGCCTGCCT GGTGCTGGTC
    801 ATTGTTCTGC TCTACTTCAG CCTATGGAAG GGAGTAAAGA CCTCAGGGAA
    851 GGTGGTGTGG ATCACAGCTA CCATGCCCTA TGTGGTCCTC ACAGCCCTGC
    901 TCCTGCGTGG AGTTACCCTT CCTGGAGCCA TGGATGGCAT CAGAGCATAC
    951 CTCAGTGTGG ACTTCTACCG ACTCTGTGAG GCATCTGTGT GGATCGATGC
   1001 TGCCACCCAG GTGTGCTTCT CCCTCGGCGT TGGGTTTGGA GTGCTGATTG
   1051 CCTTCTCCAG TTACAATAAA TTCACCAATA ACTGCTATAG AGACGCAATC
   1101 ATCACCACCT CCATTAACTC CCTGACAAGC TTCTCCTCTG GCTTCGTCGT
   1151 CTTCTCCTTC CTGGGGTATA TGGCACAGAA GCACAATGTG CCCATCAGAG
   1201 ATGTGGCCAC AGATGGACCT GGGCTCATCT TCATCATCTA TCCTGAGGCG
```

FIG. 2A

```
1251 ATCGCCACAC TCCCGCTGTC TTCTGCCTGG GCTGCTGTCT TCTTCCTCAT
1301 GCTGCTCACT CTGGGTATCG ACAGTGCAAT GGGGGGCATG GAGTCAGTGA
1351 TCACTGGGCT CGTCGATGAG TTCCAGCTGC TACATCGGCA TCGAGAGCTC
1401 TTCACTCTTG GCATTGTCCT GGCTACTTTC CTGCTGTCTC TCTTCTGCGT
1451 CACCAACGGT GGCATCTACG TCTTCACACT GCTGGACCAC TTTGCAGCTG
1501 GCACATCTAT CCTCTTTGGC GTGCTCATTG AAGCCATTGG GGTGGCCTGG
1551 TTCTACGGCG TCCAGCAATT CAGTGATGAC ATCAAGCAAA TGACAGGGCA
1601 GCGACCCAAC CTGTACTGGC GGCTATACTG AAGCTGGTC AGCCCCTGCT
1651 TCCTCCTGTA TGTGGTCGTG GTCAGCATTG TGACCTTCAG ACCCCCACAC
1701 TATGGGGCCT ACATCTTCCC AGACTGGGCC AATGCCCTGG GCTGGATCAT
1751 CGCCACATCC TCCATGGCCA TGGTGCCCAT TTATGCGACC TACAAGTTCT
1801 GCAGCCTGCC GGGGTCCTTC CGGGAGAAAC TGGCCTATGC CATCACACCT
1851 GAGAAAGACC ATCAGCTAGT GGACAGAGGG GAGGTGCGCC AATTCACGCT
1901 GCGTCACTGG CTGTTGCTGT AAAGTGGAAG GAGACAGCTG CCAGCTGGGC
1951 CACCTCACAA CAGCGGGGAC AGGGAGATCG CAAAGGAAAC CCACGAGTCA
2001 AGAAAGGAAG GAGGGCCACT TCCATGCTTC TCCTTTGTCG TACGGAAAAA
2051 TAATCGAAGC ATGGGCTTCA ACCTTTGACT GTTCACACCC AAATCATTGC
2101 CACAAAGAAG CCTCTGTCTG TGTATGGCTG TAAAAACATA CACCTCTACA
2151 CAGTGAGGTC AACAATGTCC CTGTCCCTAC TGGGTGGGAA AACCCTAGCT
2201 GGTATCCTGT CCCTGCAAGG CTGACTCCCC CATCTGTGGT CACTCTGGGA
2251 GAACAGGTCA TACTGCCCCC TGAATTCTAG AAGGACCTTG GTACCTGTAC
2301 ATACACTGTG CCAGAATCCT TGTGCTCACA GTAGTTGCCT AAACCAATTC
2351 TGTTGCTTAC ATTTACAGTG TCAAGTATCC TATTTTGCTG TTGGTAGAAA
2401 AGACAGTTAA TACATGCCAA GTCCTTTCCT GGTGCTTGGC TCCGAGCAGA
2451 CACCTTAGCA TTCTGTTCAC ACATTACACA CACACACACA CACACACACA
2501 CACACACACA CACACACACA CACACGGTCT GTTCTGAGCC ACGGAGGACA
2551 AGGGACTTGG TGCAAGTGAC CAGAGATTAT GTTTTTCCTT TATAGATGAG
```

FIG. 2B

```
2601  ATAAATAAAA TTCGTGAAAT AAGGTTGGGA GACACACCCT ACCCCTGGCC
2651  CCTGGAAGGC TGGTCAGCT TGCAGCCACT TTAGTATGGA CTTGTAGGCC
2701  ACATAAAAAG TGTACTCTTC ATAGTCAGTG TGTCCTCACC TTCTGGACAC
2751  CTGCTCTGCA CAGGGTCTCG AGATAACTTG AAGACCATAT TCTTGGCCTA
2801  GAGCCCTACC TGGTCTTCAA GGAAAGACAC CCACTGTAGG GTTTGATTTC
2851  CTACTGGCTC CTGTCACATC AATGGACATT ATCCATGTTA TAAATGACTT
2901  TTTAAAACCA TATTTATGTG TGAATCGAAC TTACTCTCAA AATGCAAGGT
2951  TAGTTTGTTC AAATCCATTT GCTGAAGAGT AATTAGTGTA AGAGGAAGGT
3001  ATGCCAAGAA TCACCTTCTT CCCGGAGCAC TGGCTTTAGT TCCTGGAGTG
3051  AAAAGTGGAT GTCATGATTT TCCTTGAGCT AATAAATGCA AACTTTGGCC
3101  TGGCCTGTGT CCTATATAAG TGGCACCATG TGTCTCCCTG AGAGAGAGTC
3151  AACCTTAGTA TTCTCTGCAA GTATACATTG GCACGAGGGT GTTAAATGTG
3201  CTACCAGGGT GTTAAATGCA GGCTGTTGG CTTTGAGACT GTAGTATGGC
3251  AGAGAAGGCT CCGGTTTACC ATCTCTCAGA GGAGTGGCTC CATGTAGACA
3301  TCCAGGTGTT GTAAGCATCT GTTTTTGTG TCTATAGCCA GTACCTTGTG
3351  TGGGTTCTTA CAAACAATAA AGAAATATA TGTTGGAAAA AAAAAAAGGA
3401  ATTC                                                3'
```

CDNA ENCODING A DOPAMINE TRANSPORTER

FIELD OF THE INVENTION

The present invention relates to a polypeptide which confers upon cells the ability to import dopamine and related compounds form the extracellular environment into the cells.

DESCRIPTION OF RELATED ART

Scientific publications described in this application are incorporated by reference thereto.

Dopamine transporters act to terminate dopaminergic neurotransmission by sodium- and chloride- dependent reaccumulation of dopamine into pre-synaptic neurons (L. L. Iversen, in Handbook of Psychopharmacology, L. L. Iversen, S. J. Iversen, & S. H. Snyder, Eds. (Plenum, N.Y., 1976), pp. 381-442; M. J. Kuhar and M. A. Zarbin, J. Neurochem. 31, 251 (1978); A. S. Horn, Prog. Neurobiol. 34, 387 (1990)).

Cocaine and related drugs bind to these transporters in a fashion that correlates well with their behavioral reinforcing and psychomotor stimulant properties; these transporters are thus the principal brain "cocaine receptors" related to drug abuse (M. C. Ritz, R. J. Lamb, S. R. Goldberg, M. J. Kuhar, Science 237, 1219 (1987); J. Bergman, B. K. Madras, S. E. Johnson, R. O. Spealman, J. Pharmacol. Exp. Ther. 251, 150 (1989)). The transporters accumulate neurotoxins with structural features resembling dopamine; their ability to concentrate the parkinsonism-inducing toxin MPP+ (1-methyl-4-phenylpyridinium) is key to this agent's selective dopaminergic neurotoxicity (S. H. Snyder, and R. J. D'Amato, Neurology 36(2), 250 (1986); S. B. Ross, Trend. Pharmacol. Sci. 8, 227 (1987)). Studies of the dopamine transporter protein suggest that it is an 80 kDa glycoprotein, but have not yet yielded protein sequence data (D. E. Grigoriadis, A. A. Wilson, R. Lew, J. S. Sharkey & M. J. Kuhar, J. Neurosci. 9, 2664 (1989)). Binding of cocaine analogs such as [$^3$H]CFT to membranes prepared from dopamine-rich brain regions reveals two sites with differing affinities (F. Javory-Agid, and S. Z. Langer, Naunyn-Schmiedeberg's Arch. Pharmacol. 329, 227 (1985); J. W. Boja, and M. J. Kuhar, Eur. J. Pharmacol. 173, 215 (1989); B. K. Madras et a)., Mol. Pharmacol. 36, 518 (1989); M. J. Kuhar et al., Eur. J. Neurol. 30(1), 15 (1990); M. C. Ritz, E. J. Cone, M. J. Kuhar, Life Sci. 46, 635 (1990).; D. O. Calligaro, and M. E. Eldefrawi, J. Pharmacol. Exp. Ther. 243, 61 (1987); B. K. Madras et al., J. Pharmacol. Exp. Ther. 251(1), 131 (1989); M. C. Ritz et al., J. Neurochem. 55, 1556 (1990)).

SUMMARY OF THE INVENTION

It is one object of the invention to produce a cDNA that encodes the dopamine transporter protein, a product of dopaminergic neurons that binds dopamine, cocaine and cocaine analogs and will transport dopamine and MPP+ into mammalian cells expressing it on their surface.

It is a further object of the invention to utilize the cDNA to produce cell lines that express DAT on their surface and to provide a method for the screening of compounds that influence the binding and/or transport of dopamine or cocaine to (into) the cells. Such cell lines may also find therapeutic application for treatment of diseases caused by depletion of dopaminergic cell populations.

A third object of the invention is to provide diagnostic means for assessing DAT expression in patients by DNA- or antibody- based tests and for assessing the onset or progression of disease by immunoassay of DAT degradation.

A final object of the invention is to provide a means for the creation of an electronic device for the measurement of dopamine, MPP+, cocaine or structurally similar compounds in samples.

These and other objects are accomplished by providing a cDNA encoding the dopamine transporter protein and a purified polypeptide conferring upon cells the phenotype of dopamine uptake from the surrounding extracellular medium. Further, the invention is embodied in cell lines, created by stable transformation of cells by a vector encoding the dopamine transporter protein, expressing the dopamine transporter protein on their surface. Another aspect of the invention relates to a method of using such lines to screen pharmaceutical compositions for their ability to inhibit the binding of dopamine, cocaine or analogs of these compounds to the transporter protein. Such a screening can also be accomplished by use of cells transiently expressing dopamine transporter cDNA. Other forms of the invention include biosensors comprising the dopamine transporter protein or a portion thereof, for example the attachment of DAT1 protein to a piezoelectric crystal and measurement of the response of the vibrational frequency of the modified crystal as a function of cocaine concentration. The invention also relates to diagnostic applications of the dopamine transporter cDNA and anti-DAT antibodies and to therapeutic applications of the pDAT1 cDNA.

(A) Time-course of [$^3$H]DA uptake into Xenopus oocyte injected with DAT1 mRNA or GABA transporter mRNA.

(B) Saturation Analysis. (Inset) Eadie-Hofstee plot of initial velocity data at concentrations from 30 nM to 10 μM.

FIGS. 2A-C: Nucleotide and deduced amino acid sequence of the rat dopamine transporter cDNA, pDAT1. The first nucleotide of the translation initiation codon is designated as position one, based on apparent Kozak sequences (Kozak, M. Nucleic Acids Res. 15, 8125 (1987).

Figure 3:
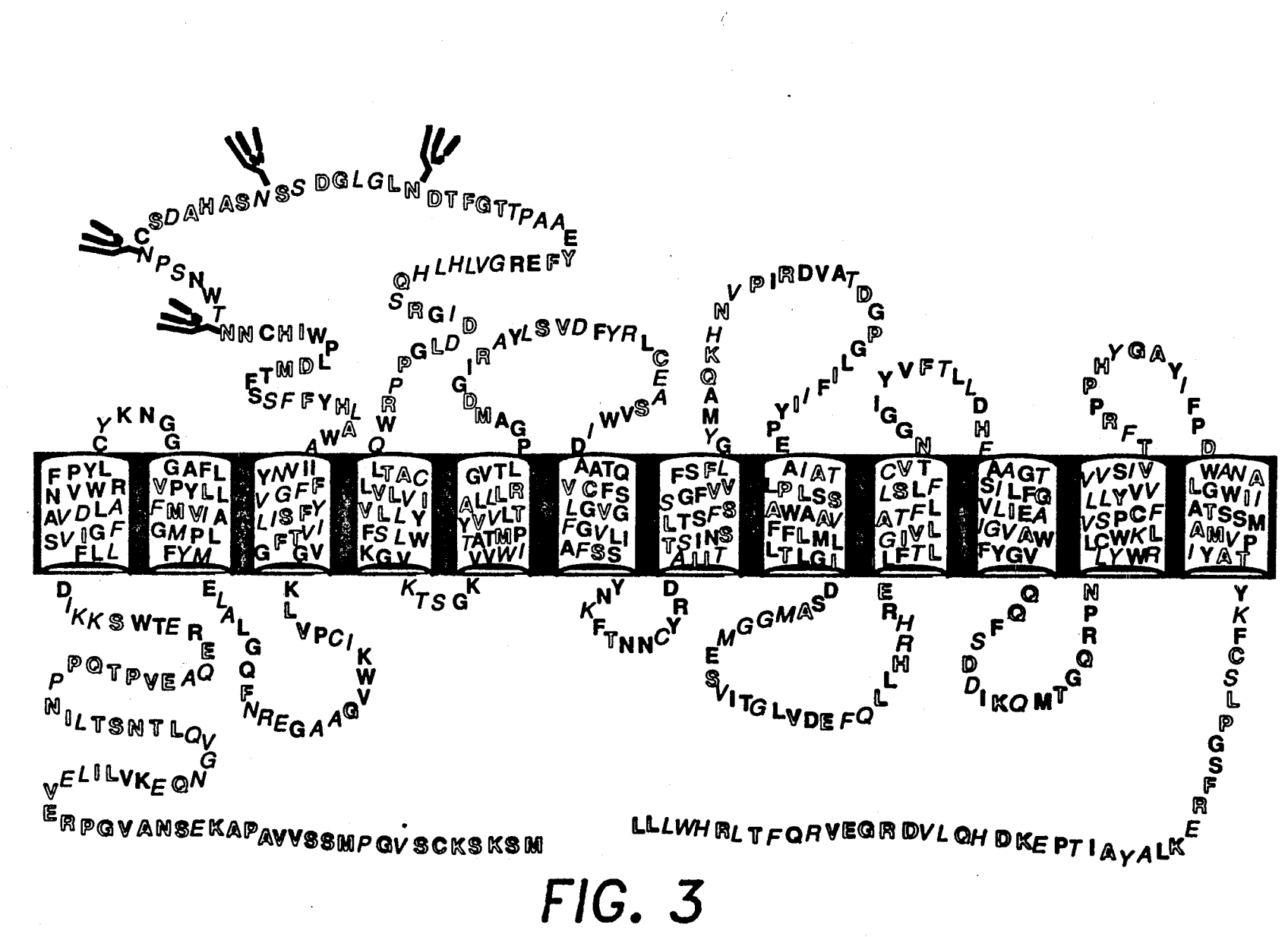

FIG. 3: Schematic representation of the dopamine transporter showing proposed orientation in the plasma membrane, amino acids conserved in GABA, dopamine and norepinephrine transporters (dark letters), amino acids conserved in dopamine and norepinephrine transporter (italic letters) or amino acids found only in DAT1 (open letters).

Figure 4:
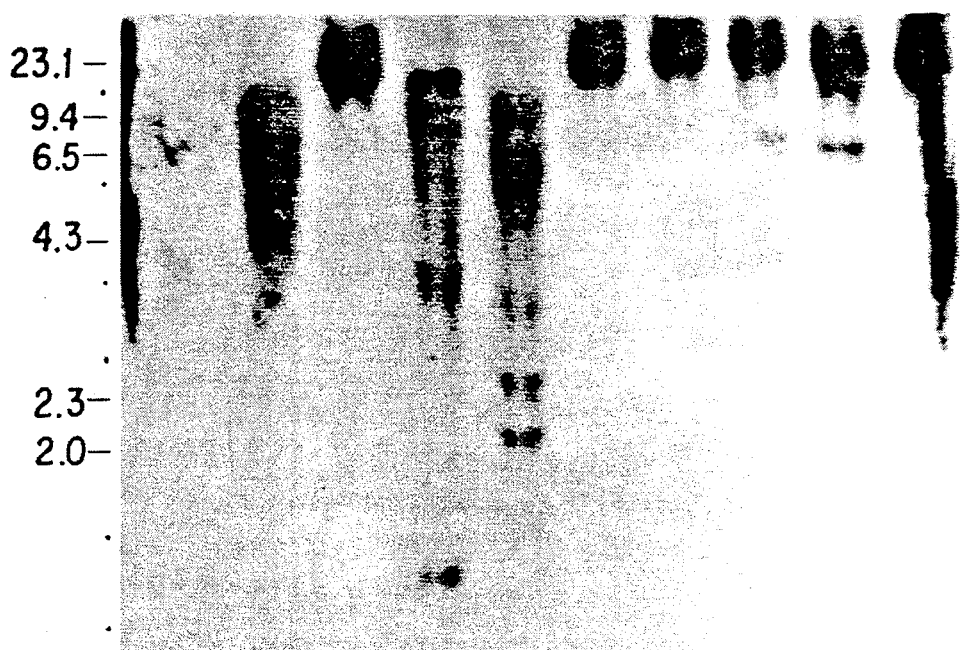

FIG. 4: Southern blot of DNA from rat using the complete DAT1 cDNA as a probe.

Figure 5:
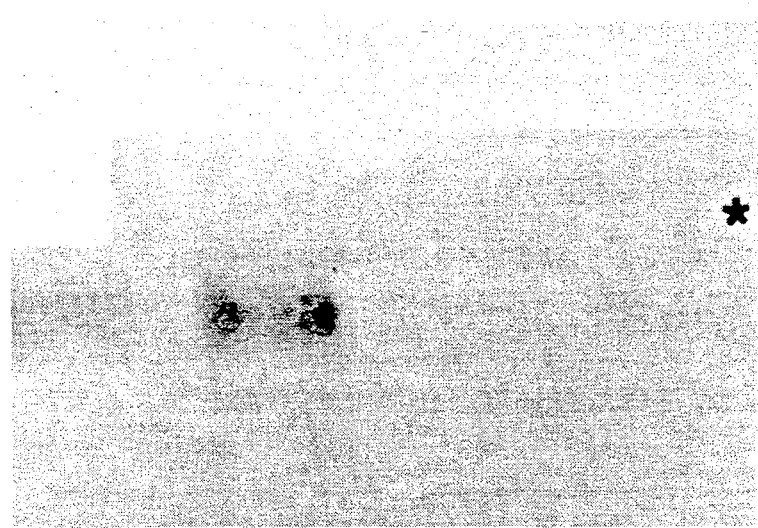

FIG. 5: Northern analysis of mRNA isolated from (l-r) midbrain, brainstem, cerebral cortex and cerebellum hybridized with radiolabelled pDAT1 cDNA. *=position of 4.4 kb RNA standard.

Figure 6:
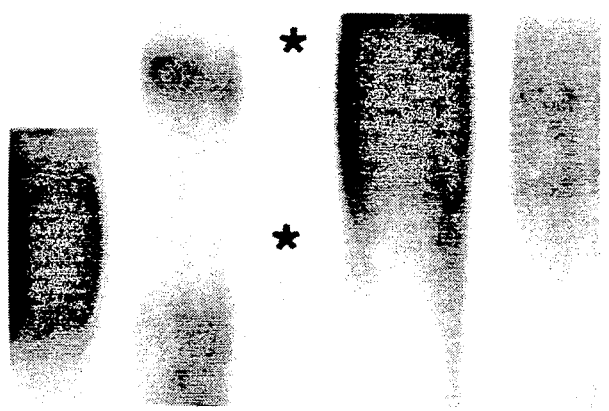

FIG. 6: SDS/PAGE autoradiogram of [$^{125}$I]DEEP photoaffinity labelled dopamine transporter expressed in (lanes 1 and 2) striatum and (lanes 3 and 4) COS cells transfected with pcDNADAT1. GBR 12909 (1 μM) was added to [$^{125}$I]DEEP labelling reactions (lanes 2 and 4) to establish controls. *=molecular weight standards, upper=110 kd, lower=84 kd.

Figure 7:
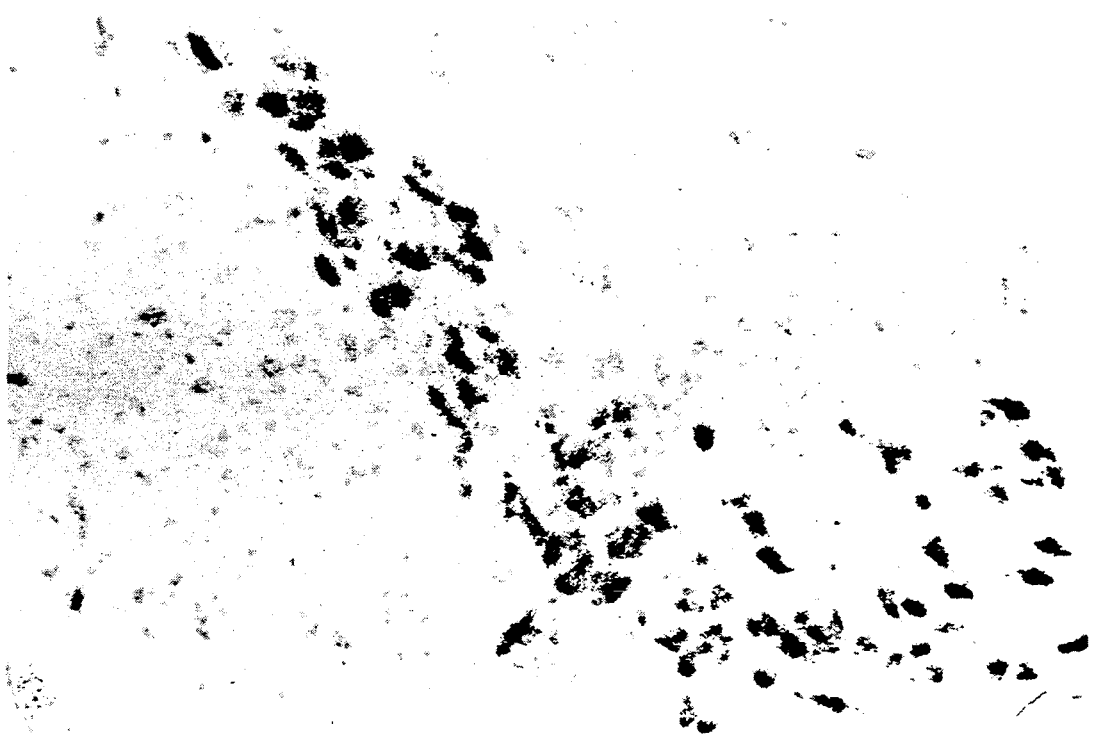

FIG. 7: Brightfield photomicrograph of in situ hybridization autoradiogram of substantia nigra (left) and VTA (right) neurons after hybridization with DAT1 cDNA.

Figure 8:
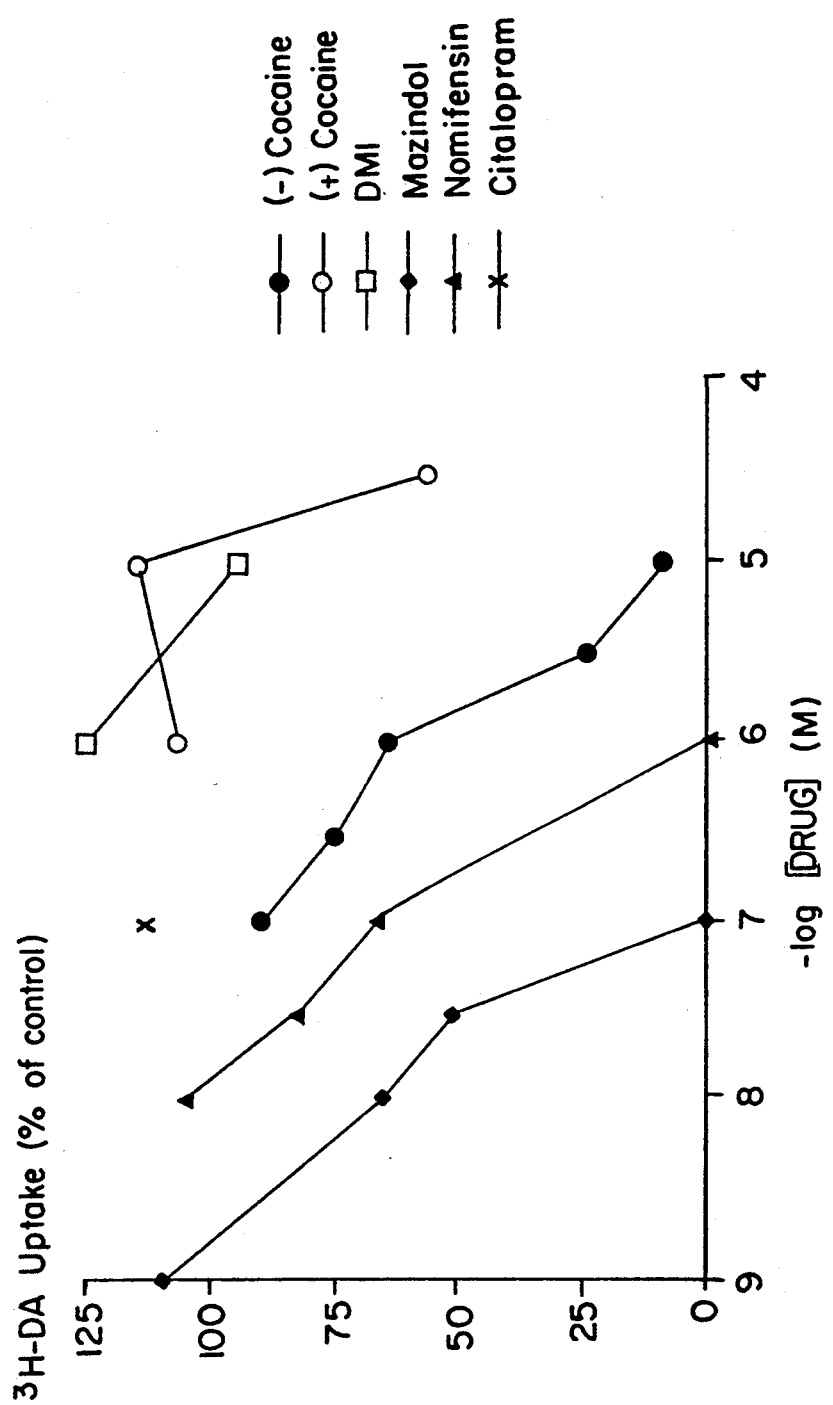

FIG. 8: Pharmacologic profile of the dopamine transporter protein expressed by microinjection into Xenopus oocytes. Abilities of various compounds to block [$^3$H]DA uptake into DAT1 mRNA injected Xenopus oocytes at different concentrations is shown. Points and bars represent mean±SEM, n=4

Figure 9:
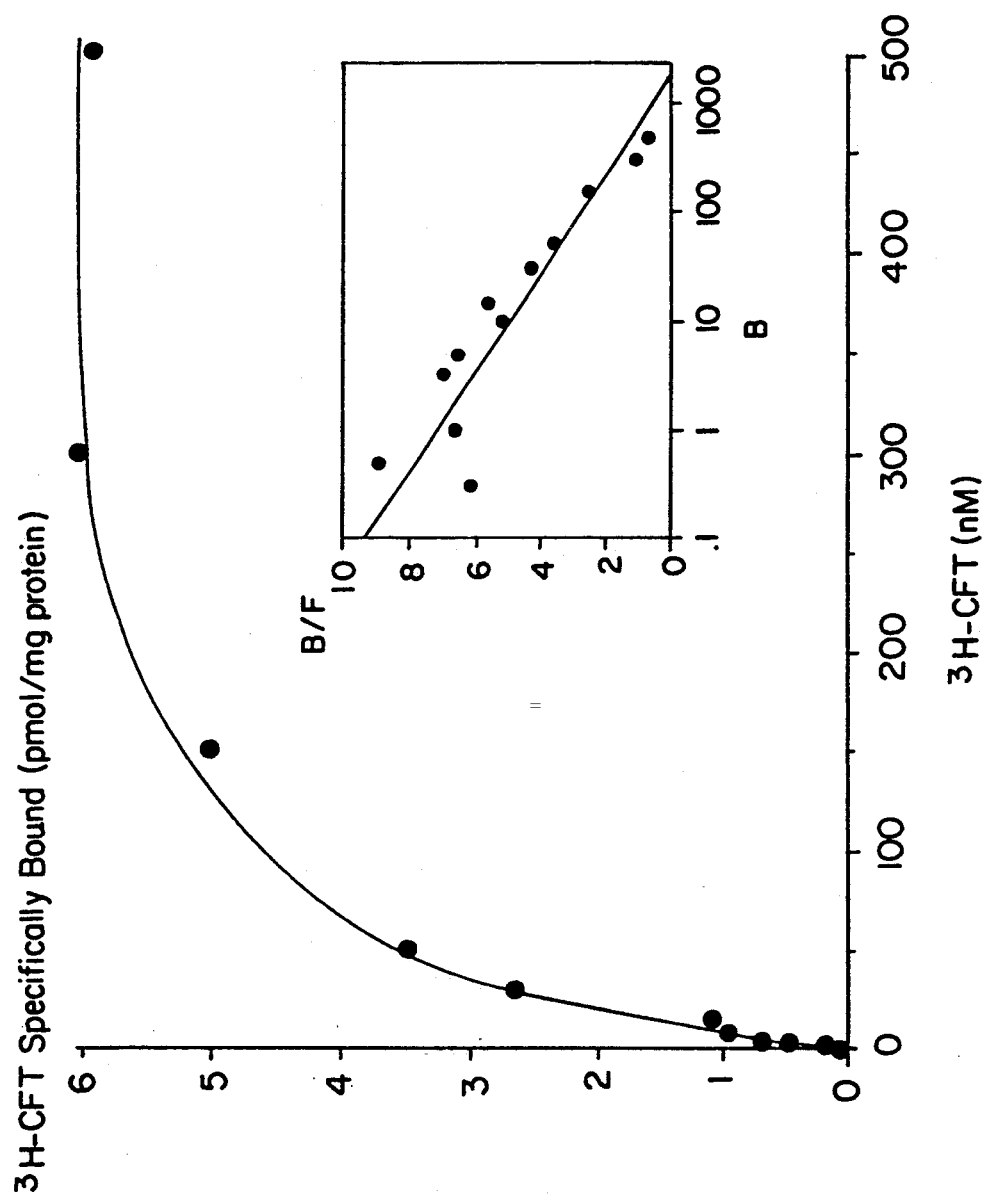

FIG. 9: Saturation analysis of [$^3$H]CFT binding to membranes of COS cells transfected with pcDNADAT1. A Representative [$^3$H]CFT saturation binding curve is presented. (Inset) Scatchard plot of the specific binding data.

Figure 10:
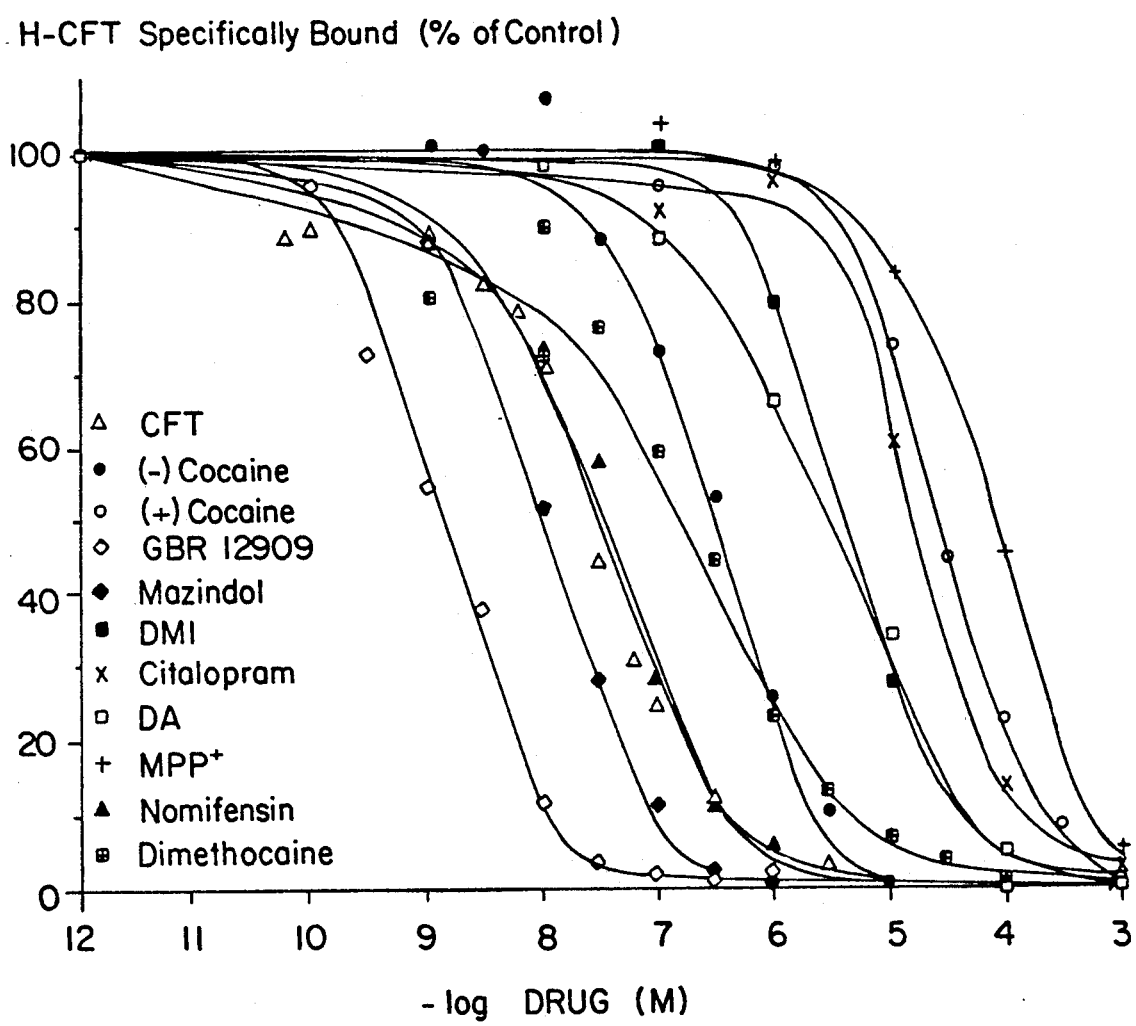

FIG. 10: Ligand competition for [$^3$H]CFT binding to cells transfected with pcDNADAT1. Results shown are the means of triplicate determinations.

Figure 11:
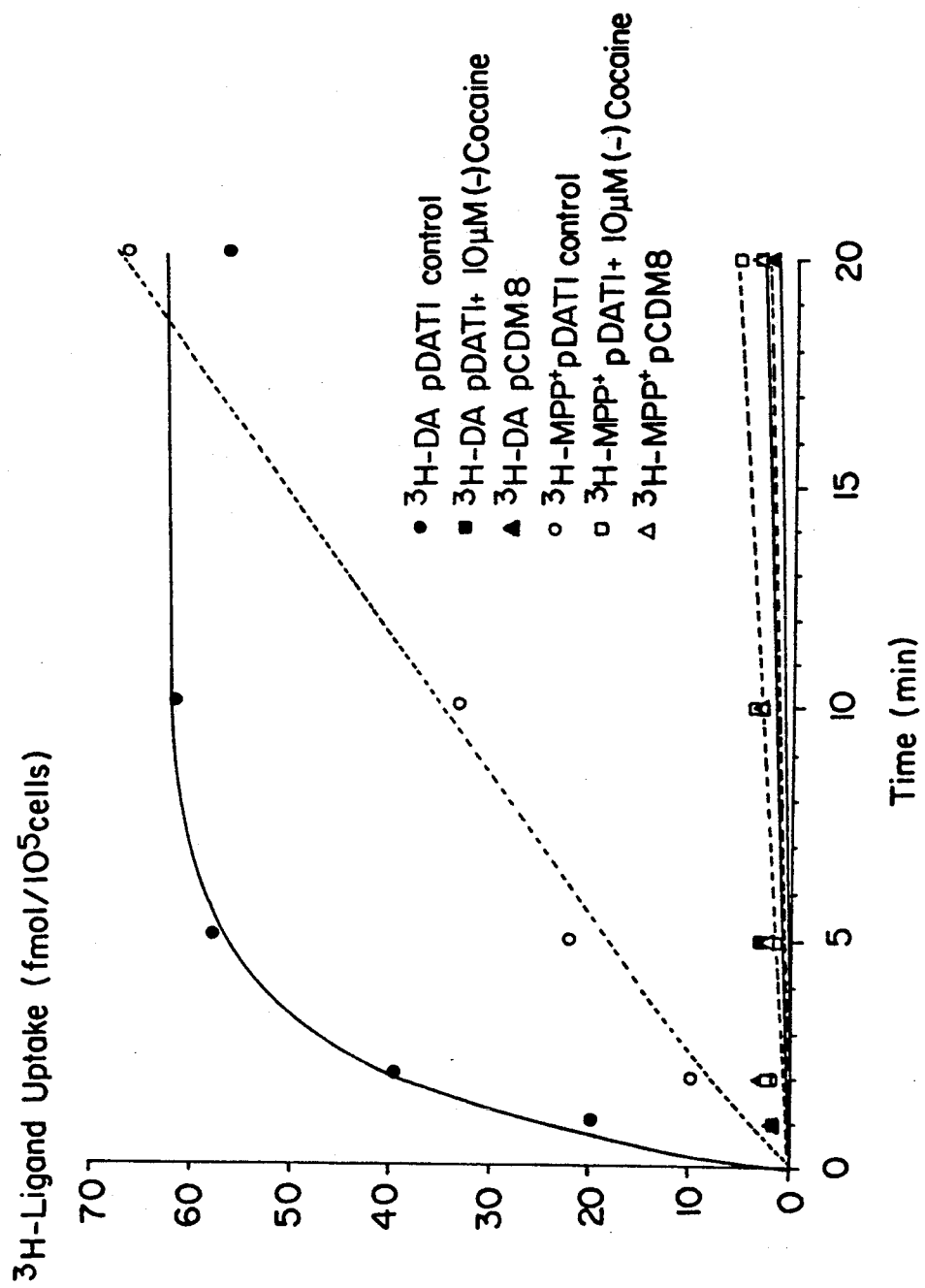

FIG. 11: MPP+ uptake in COS cells transfected with pcDNADAT1. A time-course study of [$^3$H]MPP+ and [$^3$H]DA uptake by COS cells transfected with pcDNADAT1 or vector only. Values are the means of triplicate determinations.

Figure 12:
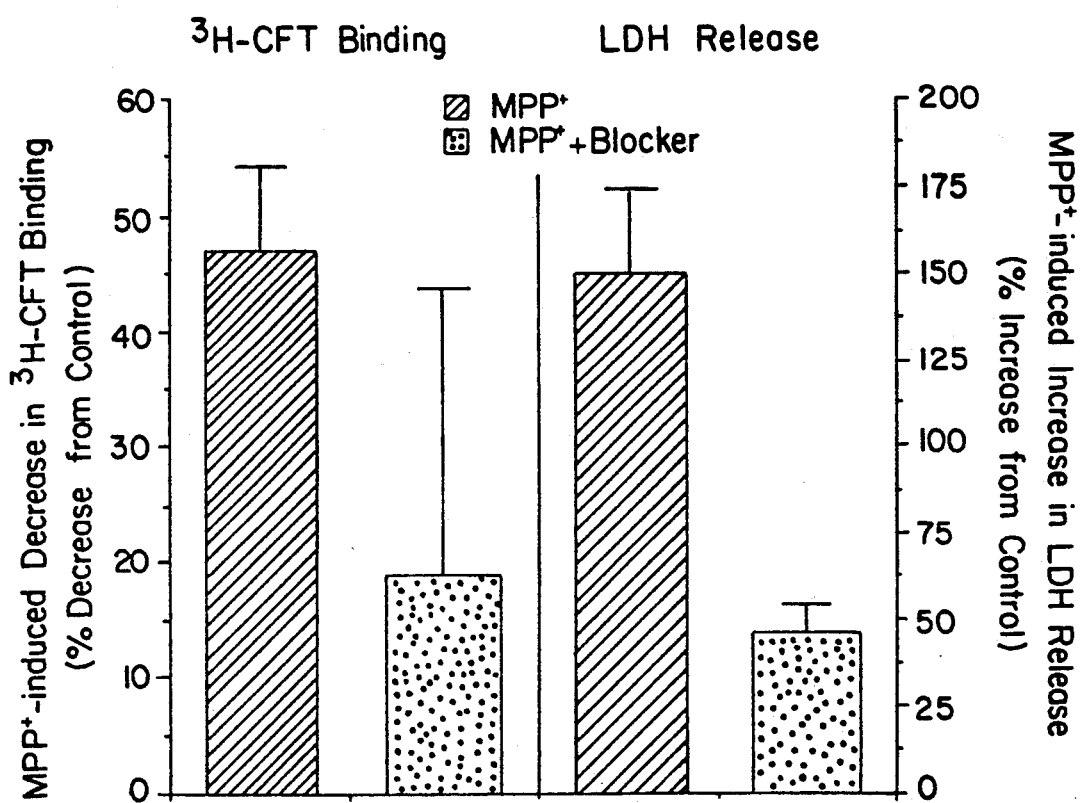

FIG. 12: MPP+ toxicity in COS cells transfected with pcDNADAT1. (Left) [$^3$H]CFT binding to membranes of pcDNADAT1-transfected COS cells treated with 1 μM MPP+ alone or in combination with 10 μM (−) cocaine. (Right) LDH activity in pcDNADAT1-transfected COS cell culture supernatants following treatments with MPP+ alone or in combination with 0.1 μM mazindol. Values represent mean±SEM, n=3.

Figure 13:
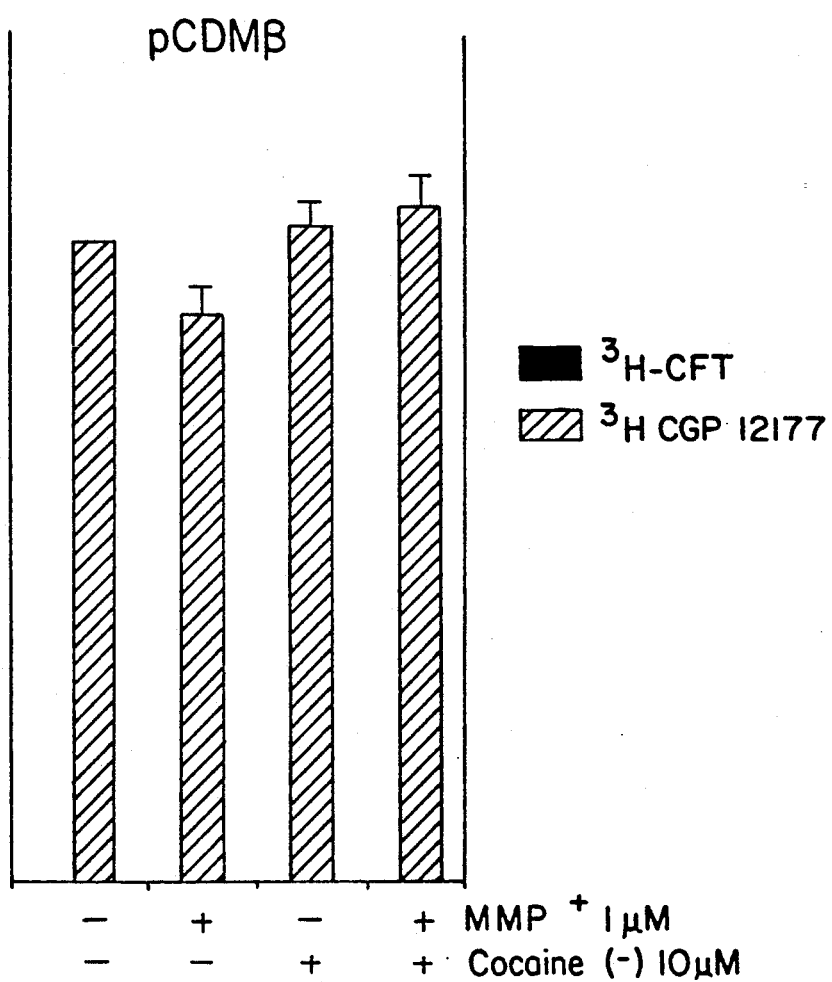

FIG. 13: LDH release from COS cells transfected with pCDMβ

Experimental conditions are as for FIG. 12, right.

DETAILED DESCRIPTION OF THE INVENTION

Recent developments encourage use of DNA homology and expression approaches to identify cDNAs encoding neurotransmitter receptor and transporter proteins. Such an approach has been used to isolate and characterize a novel cDNA, DAT1 that encodes a dopamine transporter protein. These studies demonstrate that pDAT1 can be expressed in a fashion that yields properties anticipated of brain dopamine transport, including ion dependence, pharmacology, and neurotoxin uptake (L. L. Iversen, in Handbook of Psychopharmacology, L. L. Iversen, S. J. Iversen, & S. H. Snyder, Eds. (Plenum, N.Y., 1976), pp. 381–442; M. J. Kuhar and M. A. Zarbin, J. Neurochem. 31, 251 (1978); A. S. Horn, Prog. Neurobiol. 34, 387 (1990).; S. H. Snyder, and R. J. D'Amato, Neurology 36(2), 250 (1986); S. B. Ross, Trend. Pharmacol. Sci. 8, 227 (1987)). Interactions with cocaine-related compounds document that the same molecule represents the dopamine transporter and a cocaine binding site. This transporter thus forms at least one of the sites where cocaine could exert its effects on behavioral reinforcement, since action at dopamine transporters labelled with radioactive cocaine-like drugs is the biochemical property that correlates best with behavioral reinforcement in the brain (M. C. Ritz, R. J. Lamb, S. R. Goldberg, M. J. Kuhar, Science 237, 1219 (1987); J. Bergman, B. K. Madras, S. E. Johnson, R. O. Spealman, J. pharmacol. Exp. Ther. 251, 150 (1989)). The present application thus describes the first cloned "cocaine receptor" likely to be directly involved in cocaine abuse.

DAT1 encodes a protein whose expression in COS cells produces binding displaying monophasic Scatchard plots and unitary Hill coefficients, consistent with a single binding site whose affinities match one of the [$^3$H]CFT binding sites identified in striatal membranes. This cDNA recognizes only a single mRNA in Northern analyses and a single gene in Southern analyses. These studies thus fail to provide evidence for two sites arising from the principal DAT1 gene product, for binding site heterogeneity arising from differential DAT1 mRNA splicing, or for the presence of a second very closely related gene conferring the second cocaine binding site. The second binding site could reflect a more distantly-related gene product. Alternatively it could reflect differences in post-translational processing of the DAT1 gene product such as those that have been recently identified in brain-region-specific glycosylation (R. Lew et al., Synapse 8, 152 (1991); such differences could explain the different molecular masses of DAT1 protein expressed in COS cells and the dopamine transporter expressed in the striatum.

Evidence that this transporter could play a key role in mediating the selective neurotoxicity that MPP+ can exert on dopaminergic cells of the substantia nigra and VTA includes: the dense and selective expression of DAT1 mRNA in these neurons, the rapid accumulation of MPP+ into pcDNADAT1-expressing COS cells, and the cocaine-blockable toxicity of MPP+ for expressing COS cells. Finding that expression of DAT1 can confer MPP+ sensitivity to a non-neural cell highlights the potential importance of dopamine transport for parkinsonism-inducing neurotoxic mechanisms (S. H. Snyder, and R. J. D'Amato, Neurology 36(2), 250 (1986); S. B. Ross, Trend. Pharmacol. Sci. 8, 227 (1987)).

Sequences highly conserved among GABA, norepinephrine and dopamine transporters are candidates to subserve functions shared in common among them, such as co-transport of sodium. Analysis of sequence motifs shared between DAT1 and catecholamine receptors could also lead to insights concerning amino acids involved in dopamine recognition. While not wishing to be bound by any theory of the invention, an aspartic acid residue lying within DAT1 putative transmembrane region 1, for example, could conceivably provide the interactions with the amine imputed to Asp-113 of adrenergic receptors, while the serine residues of putative transmembrane region 7 could interact with the catechol hydroxyls as ascribed to Ser-204 and Ser-207 in adrenergic receptors (C. D. Strader, I. S. Sigal, R. A. Dixon, FASEB J, 3 1825 (1989)). Data from experiments testing such ideas will enhance understanding of transporter mechanisms in a fashion that could aid in development of anticocaine and antiparkinsonian therapeutics.

The preferred embodiments of the invention are described by means of the following examples. These examples are intended to be illustrative, rather than limiting in scope. It is understood that variations in the materials and techniques described below will be apparent to those skilled in art and such are to be considered to fall within the scope and spirit of the instant application.

It is to be understood that subfragments or variants of the DAT1 protein disclosed in the present application wherein the original amino acid sequence is modified or changed by insertion, addition, substitution, inversion or deletion of one or more amino acids are within the scope of the present invention, so far as they retain the essential binding or transport specificity as mentioned above.

EXAMPLE 1

Structural and Functional Characterization of a Dopamine Transporter cDNA and the Encoded Protein A. Cloning of the cDNA for dopamine transporter by expression in Xenopus oocytes and determination of its nucleotide sequence.

Expression systems that allow assessment of whether or not a cDNA encodes a dopamine transporter have been validated, and sequences shared in common by other neurotransmitter transporters have been elucidated (T. Pacholczyk, R. D. Blakely, S. G. Amara. Nature 350, 350 (1991); J. Guastella et al., Science 249, 1303 (1990); R. D. Blakely, M. B. Robinson, S. G. Amara, Proc. Natl. Acad. Sci. USA 85, 9846 (1988); M. J. Bannon et al., J. Neurochem. 54(2), 706 (1990); G. R. Uhl et al., Mol. Brain Res. 9, 23 (1991)). These techniques have been used in this example to find cDNAs that encode members of the dopamine transporter family that are expressed in brain regions rich in dopaminergic neurons. A cDNA library was made from poly A(+) RNA from rat ventral midbrain. Ventral midbrain was dissected rapidly from 100 male Sprague-Dawley rats by removing both cerebral peduncles from a block defined anteriorly by the mammillary bodies, posteriorly by the anterior pons, and dorsally by the ventral aspect of the red nucleus. Poly (A)+ RNA was prepared by an oligo-dT column method (Fast-track, In Vitrogen), and was active in inducing uptake of [$^3$H]DA in the Xenopus oocyte assay (R. D. Blakely, M. B. Robinson, S. G. Amara, Proc. Natl. Acad. Sci. USA 85, 9846 (1988); M. J. Bannon et al., J. Neurochem. 54(2), 706 (1990); .G. R. Uhl et al., Mol. Brain Res. 9, 23 (1991)). A λZap II library with 7×10$^6$ recombinants was prepared from cDNAs migrating on agarose gel electrophoresis with motilities of more than 2.5 kb (Strategene). 5×10$^5$ plaques were screened with a $^{32}$P-end-labelled 2-fold degenerate oligonucleotide (5'TAGGGGATCAGGAAG[A/G-]CACCTCCGCCGTTCTTGTAGCACAGGT AGGGGAAGCGCCACACGTT 3' (SEQ. ID. NO. 4); putative transmembrane regions 1 and 2) whose sequences were based on sequences conserved between the norepinephrine and GABA transporters. The library was also screened with products of PCR reactions using the mixed oligonucleotide primers A and B below. The sequences are shown using the standard ambiguity code to represent degenerate choices of nucleotides (Y=C or T, M=C or A, R=G or A, S=C or G, W=A or T, I=inosine):

A (upstream, mixture of 32 sequences)   (SEQ. ID. NO. 5)
CGGGATCCAAYGTITGGMGITTYCCITAYYT B (downstream, mixture of 128 sequences)   (SEQ. ID. NO. 6)
GCGAATTCCCAGGCCRTAISWRAARAARATYTG The oligonucleotides recognize putative conserved sequences in transmembrane 1and 6 regions of these two transporters. 27 positively-hybridizing plaques were isolated, plasmid autoexcized according to the manufacturer (Stratagene technical bulletin for catalog #237211, 237511, 237611), and capped synthetic mRNA transcribed from each plasmid as described in Uhl, et al. Mol. Brain Res. 9, 23 (1991). Three synthetic RNA preparations conferred robust GABA transport into injected oocytes, 3 additional clones shared restriction map patterns that identified them as encoding GABA transporters (Guastella, J. et al., Science 249, 1303-1306 (1990)). mRNA transcribed from one rescued subclone, designated pDAT1, conferred consistent cocaine-blockable accumulation of [$^3$H]dopamine ([$^3$H]DA) that was more than 10 times background levels in the Xenopus oocyte uptake assay (the "uptake assay") but did not confer uptake of glutamate, glycine, adenosine, or serotonin. The uptake assay is performed as previously described (Uhl, G. et al. Mol. Brain Res. 9, 23 (1991). pDAT1 was subjected to restriction mapping and automated sequencing of both strands with fluorescent chain-terminator dyes (Applied Biosystems) and confirmatory sequencing by standard manual methods.

Figure 1A:
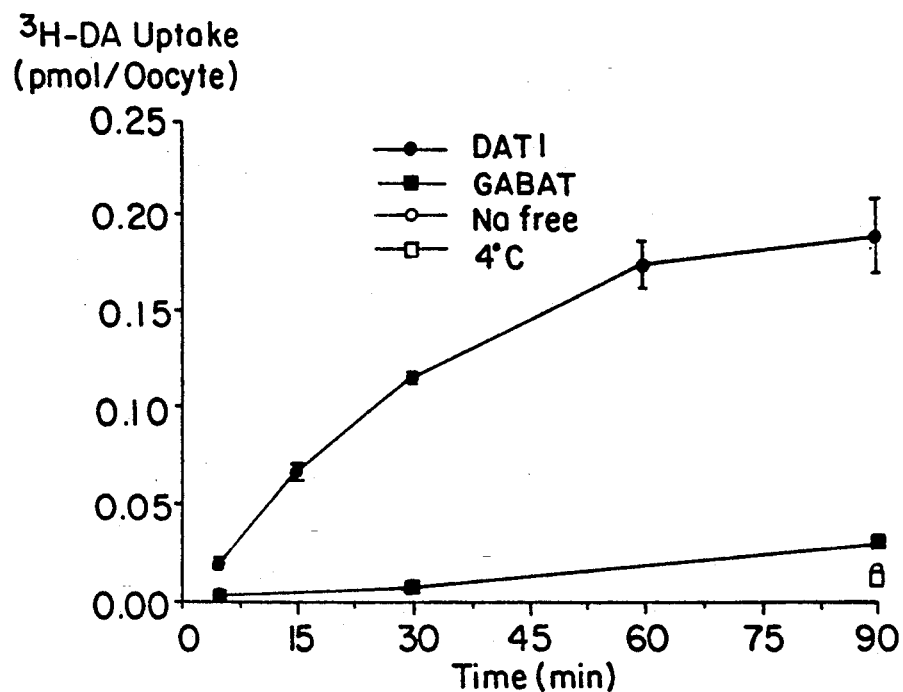
FIGS. 1A-B: Properties of [$^3$H]DA uptake into Xenopus oocytes injected with mRNA transcribed from pDAT1.

FIG. 1A shows the activity of in vitro transcripts from the pDAT1 template cDNA clone in the uptake assay compared to transcripts from a GABA transporter template and control experiments of buffer injection and assay at 4° C. No activity was observed for the injection of pDAT1 RNA at 4° C. as at this temperature dopamine transport, as for many energy dependent processes, is inhibited. Furthermore, no activity was seen if sodium-free medium was used. pDAT RNA assayed under normal conditions results in uptake of approximately 0.2 pmol of [$^3$H]DA per oocyte after 90 minutes. This is about ten-fold greater activity than GABA transporter RNA, demonstrating that the assay is specific for dopamine transporter. Injection of buffer alone defines the background level of non-specific dopamine uptake. Oocytes injected with mRNA transcribed from pDAT1 do not accumulate [$^3$H]-choline, glutamate, serotonin, GABA, glycine, or adenosine at a level above background. Inhibitors or competitors for transporters, including hemicholinium-3, dihydrokainate, nipecotate, dipyridamole, glycine and taurine fail to affect [$^3$H]DA accumulation into DAT1 expressing oocytes.

Figure 1B:
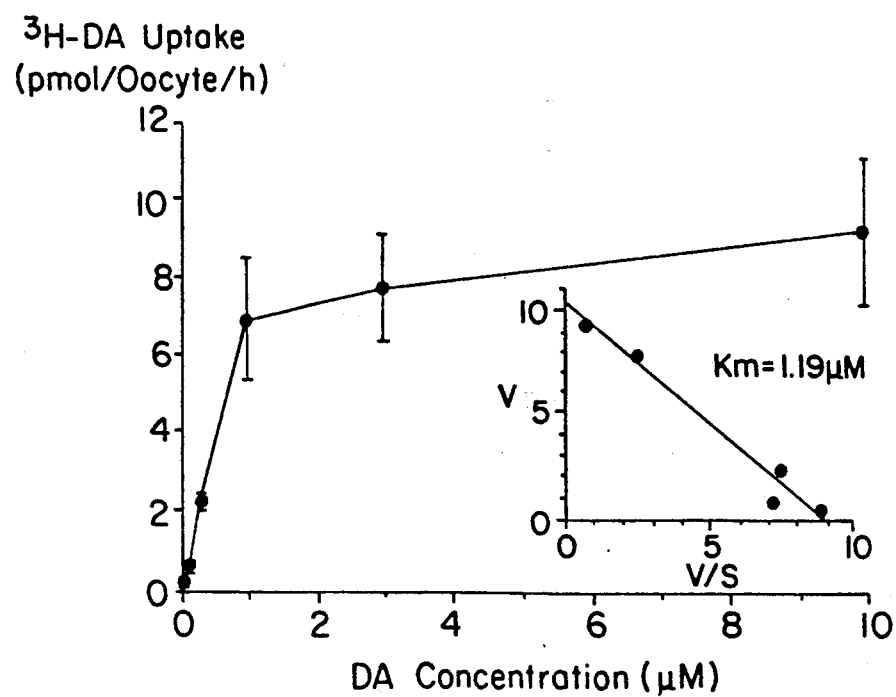

FIG. 1B demonstrates that the activity induced by pDAT1 RNA is saturable, a prerequisite for interpreting the results as being due to the expression of protein that imports dopamine by an active transport mechanism. The inset of FIG. 1B shows Eadie-Hofstee analysis of the data (Hofstee, B. H. J. Science 116, 329 (1952); Eadie, G. S., et al. J. Biol. Chem. 181, 449 (1949)), providing a $K_m$ value for the transport of dopamine by the transporter encoded by pDAT1 of 1.19 μM.

FIGS. 2A–C (SEQ. ID. NO. 1) shows the nucleotide sequence of pDAT1 cDNA and the predicted amino acid sequence of the encoded protein (SEQ. ID. NO. 2). pDAT1 contains a 3.4 kb cDNA insert with a 1857 bp open-reading frame. Assignment of the first ATG as the translation initiation site, based on resemblances to consensus sequences for translational initiation (Kozak, M. Nucl. Acids Res. 15, 8125-8148, 1987)), results in a protein of 619 amino acids with a nonglycosylated molecular mass of ca. 69 kDa. Hydrophobicity analysis reveals 12 hydrophobic segments long enough to form transmembrane domains. The predicted DAT1 protein lacks an identifiable signal sequence, consistent with a cytoplasmic N terminus localization. It displays potential sites for N-linked glycosylation (the sequence Asn-X-Ser/Thr, Marshall, R. D. Ann. Rev. Biochem. 41, 673 (1972)) at amino acid residues 181, 188, 196 and 204 FIG. 3). This sequence shows 67% amino acid identity and 81% similarity with the human norepinephrine transporter (Pacholczyk, T. et al., Nature 350, 350-354 (1991)), 45% identity and 67% similarity with the rat GABA transporter (Guastella, J. et al, Science 249, 1303-1306 (1990)), and no substantial homology with other GENBANK/NBRF sequences. The regional distribution of the identical amino acids is also striking; residues forming putative transmembrane domains are especially well conserved.

FIG. 3 presents the amino acid sequence of the dopamine transporter in schematic form showing proposed orientation in the plasma membrane. The amino acids conserved in GABA, dopamine and norepinephrine transporters (dark letters), amino acids conserved in dopamine and norepinephrine transporter (italic letters) or amino acids found only in DAT1 (open letters). Sites of potential N-linked glycosylation are designated by branches at the appropriate residues.

Southern analyses performed at moderate stringencies are consistent with DAT1 hybridizing to segments of a single rat gene of at least 20 kilobases (FIG. 4). Hybridization was performed in 0.5×SSC, 0.1% sodium dodecyl sulfate, 1×Denhardt's buffer at 52° C. overnight. The blot was washed in two changes of 0.5×SSC for one hour each at 52° C. The conclusion that the rat gene is single copy per haploid genome is based on the observation of a single band of hybridization to the DAT1 probe for digests using ClaI, NotI, PvuI, SalI, SmaI and XhoI and sets of bands that add up to approximately 30 kilobases for digests using BamHI, EcoRI and HindIII.

B. Identification of the dopamine transporter encoded by pDAT1 in vivo.

Dopaminergic neurons of substantial basic and clinical interest reside in the basal midbrain (Iversen, L. L. in "Handbook of Psychopharmacology", pp. 381–442, eds. Iversen, L. et al., c. 1976 by Plenum, New York, N.Y.). Northern blot analysis of DAT1 expression in these brain regions was performed as follows: 1 μg (midbrain) or 2 μg (other regions) poly (A)+-selected RNA prepared from rat tissues that were rapidly dissected and frozen was electrophoresed along with molecular weight standards (BRL) and transferred to nylon membranes that were hybridized with $^{32}$P-random-priming-labeled Not I/Sal I fragment of pDAT1 in 5×SSPE/1% SDS/50% formamide/2.5×Denhardt/200 μg/ml herring sperm DNA at 42° C. overnight, washed twice in 0.4×SSC/0.5% SDS for 30 min at 52° C., and exposed to Kodak XAR film for 2 days at −70° C. using an intensifying screen. FIG. 5 shows that mRNA extracted from midbrain and from brainstem preparations that contain this region reveals a single band with a mobility corresponding to a size of 3.7 kb. This mRNA is not found in several peripheral tissues or other brain regions.

Transporter expressed from the mRNA can be covalently labelled with the photoaffinity label [$^{125}$I]DEEP in a GBR 12909-blockable fashion (Grigoriadis, D. E. et al., J. Neuroscience 9, 2664 (1989)). COS cells were transfected with pcDNADAT1 and membranes prepared by disruption of cells with a polytron homogenizer (setting 8, 30 seconds) in 50 mM Tris pH 7.4, 120 mM NaCl. Membranes were pelleted at 48,000× g for 10 minutes, resuspended in the same buffer, centrifuged again as above, then resuspended in homogenizing buffer and aliquotted for use (Madras, B. K. et al. Mol. pharmacology 36, 518 (1989)). 100 μg COS cell or 40 μg rat striatal membrane protein were incubated at 4° C. in dark conditions with 1 μM [$^{125}$I]DEEP (New England Nuclear) with or without 1 μM GBR 12909 (Research Biochemicals International, Waltham, Mass.), flashed with UV light, concentrated by centrifugation, and solubilized with Laemmli DS/PAGE buffer. Proteins resolved on 10% SDS/PAGE were assessed by autoradiography (Grigoriadis, D. E. et al., J. Neuroscience 9, 2664 (1989)), and compared to coelectrophoresed prestained molecular mass standards (Biorad). As shown in FIG. 6, the dopamine transporter detected transfected CO cells by this method displays a mobility on SDS/PAGE corresponding to a molecular mass of 107 kDa.

High resolution mapping of DAT1 expression in vivo was performed by in situ hybridization as follows: 10 μm cryostat sections through the midbrain of PLPG-perfused rats were hybridized with $^{35}$S-random-priming-labelled Not I/Sal I fragment of pDAT1, washed, and subjected to emulsion autoradiography with 1 week exposure as described [G. R. Uhl, Ed., In Situ Hybridization in Brain (Plenum, N.Y., 1986)]. Similar results were obtained using radiolabelled oligonucleotides directed toward specific portions of DAT1 sequence (SEQ. ID. NO. 3). In situ hybridization reveals hybridization densities overlying neurons of the substantia nigra and ventral tegmental area (VTA) although some neurons are much more lightly labelled (FIG. 7).

3. Pharmacologic profile of the protein expressed by the pDAT1 cDNA

The relative potencies of cocaine-like drugs in inhibiting [$^3$H]DA uptake in oocytes expressing DAT1 fit well with their relative potencies at the dopamine transporter identified in brain synaptosomes (FIG. 8) (L. L. Iversen, in Handbook of Psychopharmacology, L. L. Iversen, S. J. Iversen, & S. H. Snyder, Eds. (Plenum, New York, 1976), pp. 381–442; M. J. Kuhar and M. A. Zarbin, J. Neurochem. 31, 251 (1978); A. S. Horn, Prog. Neurobiol. 34, 387 (1990).; J. Hyttel, J. Prog. Neuropsychopharmacol. Biol. Psychol. 6, 277 (1982); J. A. Javitch, R. O. Blaustein, S. H. Snyder, Mol. Pharm. 26, 35 (1984); P. Berger et al., Eur. J. Pharmacol. 107, 289 (1985); H. Schoemaker et al., Arch. Pharmacol. 329, 227 (1985)). The more active minus isomer of cocaine is almost two orders of magnitude more potent than the plus isomer. Mazindol displays a potency higher than that of cocaine, and agents primarily active at norepinephrine and serotonin transporters, desmethylimipramine (DMI) and citalopram, show negligible potency (L. L. Iversen, in Handbook of Psychopharmacology, L. L. Iversen, S. J. Iversen, & S. H. Snyder, Eds. (Plenum, N.Y., 1976), pp. 381–442; M. J. Kuhar and M. A. Zarbin, J. Neurochem. 31, 251 (1978); A. S. Horn, Prog. Neurobiol. 34, 387 (1990)). Drug inhibition studies of dopamine uptake were performed using the oocyte uptake assay described above with the modification that the drug to be tested is added with the labelled dopamine at various concentrations. Inhibition is indicated by a reduction in DA uptake as the inhibitor concentration is increased.

Transiently transfected COS cells were also utilized to investigate the pharmacologic profile of expressed DAT1. COS cells were transfected with pcDNADAT1 by electroporation, cultured for 2-3 days, washed with Hank's solution, frozen and stored at −70° C. Membranes were prepared by polytron disruption and centrifugation, incubated with [³H]CFT (82.7 Ci/mmol NEN) at 4° C. for 2 h in 500 μl of 50 mM Tris, 120 mM NaCl pH 7.4, aspirated over GF/B filters presoaked with 0.05% polyethlenimine using a Brandel cell harvester, and washed three times with 3 ml of ice-cold buffer. Saturation assays used 0.1–500 nM [³H]CFT and bound [³H]CFT was assessed by liquid scintillation counting, non-specific binding was defined as binding in the presence of 30 μM (−) cocaine, and data was analyzed with EBDA and LIGAND as described [P. J. Munson, and D. Rodbard, Anal. Biochem. 107, 220 (1980); G. A. McPherson, J. Pharmacol. Method. 14, 213 (1985)]. Binding was linear with tissue concentration over ranges of 50–300 μg/tube. The COS cells transfected with DAT1 cDNA display binding of [³H]CFT ([³H]2β-carbomethoxy-3β-(4-fluorophenyl)-tropane) with $K_D$ 46.5±7.8 nM and $B_{max}$ 6.0±1.3 pmol/mg protein (n=6). Scatchard analyses reveal a single site; Hill slopes are 1.02±0.06 (n=4) (FIG. 9). Binding can be displaced by cocaine stereoisomers, GBR 12909, mazindol and CFT with affinities that correlate well (r=0.96, p<0.0001) with their affinities for striatal dopamine transporters (FIG. 10) (J. Hyttel, J. Prog. Neuropsychopharmacol. Biol. Psychol. 6, 277 (1982); J. A. Javitch, R. O. Blaustein, S. H. Snyder, Mol. Pharm. 26, 35 (1984); P. Berger et al., Eur. J. Pharmacol. 107, 289 (1985); H. Schoemaker et al., Arch. Pharmacol. 329, 227 (1985). F. Javory-Agid, and S. Z. Langer, Naunyn-Schmiedeberg's Arch. Pharmacol. 329, 227 (1985); J. W. Boja, and M. J. Kuhar, Eur. J. Pharmacol. 173, 215 (1989); B. K. Madras et al., Mol. Pharmacol. 36, 518 (1989); M. J. Kuhar et al., Eur J. Neurol. 30(1), 15 (1990); M. C. Ritz, E. J. Cone, M. J. Kuhar, Life Sci. 46, 635 (1990)). Compounds which demonstrate displacement of [³H]-labelled CFT binding from expressed DAT and/or striatal membrane preparations are considered "functionally equivalent cocaine analogs".

Transfected COS cells display avid uptake of [³H]DA and [³H]MPP. (FIG. 11). For this experiment, 2–3×10⁴ COS cells transfected with pcDNADAT1 were plated in 35 mm dishes in 2 ml of DMEM containing 10% FBS, cultured for 2–3 days, and incubated with 5 nM [³H]MPP+ (83.9 Ci/mmol, NEN) or 10 nM [³H]DA (50.0 Ci/mmol, NEN) in Krebs-Ringer-HEPES (KRH) buffer at 37° C. Uptake was terminated by three washes with ice-cold KRH, radioactivity was extracted with 2N NaOH and measured by scintillation counting. Dopamine and MPP+ uptakes are rapid, sodium and chloride dependent, and cocaine blockable (L. L. Iversen, in Handbook of Psychopharmacology, L. L. Iversen, S. J. Iversen, & S. H. Snyder, Eds. (Plenum, New York, 1976), pp. 381–442; M. J. Kuhar and M. A. Zarbin, J. Neurochem. 31, 251 (1978); A. S. Horn, Prog. Neurobiol. 34, 387 (1990).; J. A. Javitch, R. J. D'Amato, S. M. Strittmatter S. M. Snyder, Proc. Natl. Acad. Sci. USA 82, 2173 (1985)), although [³H]DA uptake reaches peak values more rapidly than [³H]MPP+ accumulation.

COS cells expressing DAT1 demonstrate sensitivity to MPP+. COS cell cultures were transfected with pcDNADAT1 as described above, grown in normal medium for 24 hours, changed to medium containing test drugs or normal control conditions for 15–20 h, and then harvested. Cells were subjected to [³H]CFT binding as described above, and cells and medium assayed for LDH activity as described (P. G. Cabaud & F. Wroblewski Am. J. Clin. Path. 30, 234 (1958). Values presented represent the percent by which normalized [³H]CFT binding was reduced from control culture values, and the percent by which normalized LDH values released into the medium increased as a fraction of total (plate plus medium) LDH values. Expression of DAT1 confers MPP+ toxicity on transfected COS cells. 1 μM MPP decreases [³H]CFT binding and increases released lactate dehydrogenase (LDH) when applied to pcDNADAT1-expressing cultures for 15–20 hours (FIG. 12). Changes in each of these two markers are almost absent when 10 μM (−) cocaine or 0.1 μM mazindol is coapplied with the MPP+. MPP+ fails to enhance LDH release from cells or reduce binding of [³H]CGP 12171, a beta adrenergic receptor ligand, in parallel COS cell cultures transfected with pCDMβ, a beta adrenergic receptor expression plasmid (J. C. Schaeffer, C.-L. Lin, S. Kitayama, G. R. Uhl, Mol. Brain Res. 9, 271 (1991)) (FIG. 13).

EXAMPLE 2

Creation of Permanent Cell Lines Expressing DAT1 at the Cell Surface

Insertion of DAT1 cDNA into a constitutive mammalian expression vector and stable tranformation of COS cells.

The DAT1 cDNA was purified as a NotI/SalI fragment from the bluescript plasmid pDAT1 and inserted into the eukaryotic expression vector pCDNA1 to form the plasmid pCDNA/DAT1. COS cells (other cell lines may be used as well) were transfected with pCDNA/-DAT1 by electroporation, as described in detail in (Schaeffer et al., Mol. Brain Res. 9: 271–276, 1991), with or without eqimolar amounts of pRSVNEO (Goodman, C. in DNA Cloning: A Practical Approach vII. D. Glover, (Ed), Washington, IRL Press, 1985 pp 143–90) cotransfectants and cells (COS7) stably integrating neomycin resistant clones are selected by growth for three weeks in the antibiotic G418 (200–600 μg/ml) as described (Goodman, op cit). At the end of four weeks, individual cells are isolated, colonies grown, and colonies assayed for DAT1 expression by growth on polyester filters and binding to tritiated [³H]CFT as described (Schaeffer et al., Molecular Brain Research 9: 271–276, 1991). Positively-expressing clones are then assayed for MPP+ toxicity and ³H CFT binding in membrane homogenate preparations as described above.

EXAMPLE 3

Expression of DAT1 Protein in *Escherichia coli* and Purification of the Bacterially Expressed Protein 1. Any of several expression systems can be utilized to obtain DAT1 protein expression in *E. coli*. For example, the plasmid vector pFLAG system (International Biotechnologies, Inc., New Haven, Conn.) produces the polypeptide of interest attached to a short protein sequence that allows purification of the fusion protein by use of a monoclonal antibody directed against a hydrophilic, and thus surface localized, octapeptide. The open reading frame portion of the DAT1 cDNA is obtained by SalI digestion and purification of the 2.9 kilobasepair fragment by electrophoresis and elution from an agarose gel by standard techniques and cloned into the SalI site of the pFLAG vector (International Biotechnologies, Inc.) to obtain the plasmid pCKS-2. The appropriate *E. coli* host is transformed and colonies containing the DAT1 cDNA may be screened by colony hybridization using the DAT1 cDNA as probe. Positive clones are grown as large-scale cultures and the fusion protein is obtained in pure form by use of the monoclonal antibody affinity column as described by the manufacturer of the system, except that the elution buffer is modified by the addition of 0.5% CHAPS (3-[(3-Cholamidopropyl)-dimethylammonio]1-propanesulfonate). Authentic DAT protein lacking the FLAG octapeptide is obtained by enterokinase cleavage of the fusion protein as described by the supplier of the FLAG system.

EXAMPLE 4

Purification of DAT from Tissues or from Transformed Mammalian Cells

As protein isolated from transformed bacterial cells lacks post-translational modifications, such as sugar additions, that occur in mammalian cells, the purification of the protein from transformed COS cells is discussed.

COS cells transformed as described in Example 2 are subjected to a purification protocol as described for the purification of the GABA transporter (Radian, et al., J. Biol. Chem. 261, 15437–15441 (1987) with the modification that binding of labelled CFT is used to assay for the presence of DAT in the sample rather than labelled gamma-amino butyric acid. The protocol is modified as required to allow the isolation of DAT as a distinct protein by techniques known to a practitioner of the art.

EXAMPLE 5

Diagnosis of Gene Variants in the Dopamine Transporter Locus by Southern Blotting DNA isolated from white blood cells by standard protocols (e.g. Sambrook, J. et al. "Molecular Cloning, A Laboratory Manual", 2nd edition, pp. 9.14–9.23, c. 1989 by Cold Spring Harbor Laboratory Press, Cold Spring Harbor, N.Y.) is analyzed by Southern blots using a number of restriction enzymes showing relatively high frequency of population variants, and stringencies defined by conditions as described above for Southern blotting. Restriction fragment length polymorphisms (RFLPs) in this locus can then be examined for their distribution in a sample of 20 caucasian and 20 black controls free of substance abuse, and 20 caucasian and 20 black individuals with histories of substance abuse. Any restriction fragment length polymorphic forms of the gene found in higher abundance in drug abusing compared to nondrug abusing populations are checked by ascertainment in other populations. Similar strategies are applied to patients with Parkinson's disease and control patients.

EXAMPLE 6

Diagnosis of Deficiency, Mutant or Overexpression of Dopamine Transporter by PCR 1. mRNA obtained from tissue biopsy from a patient is converted subjected to quantitative reverse-transcript PCR (for example, see A. M. Wang, et al. PNAS USA 86:9717 (1989)) utilizing as primers oligonucleotides derived from the cDNA sequence of DAT1. Use of the 5' 17-mer, AGGAGTCAGTCGAAGAA, bases 10 through 27 of FIG. 2A (SEQ. ID. NO. 1) as the upstream primer and TAAGAACCCACACAAGG, the reverse complement of bases 3344 to 3360 of FIG. 2C (SEQ. ID. NO. 1) as the downstream primer allows examination of the character of the entire DAT1 mRNA. Variance in the expression level can be ascertained by comparison of product yield with a normal control. Abnormal mRNA structures can be diagnosed by observation of a product band of a length different from the normal control. Point mutants can be observed by use of primers and conditions appropriate for detection of the mismatch between the mutant and normal alleles. For example, the "reverse dot blot" procedure for screening the expression of several mutant alleles in a single experiment, which has been described for the CFTR gene, mutants of which cause cystic fibrosis (Erlich, H. A., et al Science 252:1643 (1991).

EXAMPLE 7

Use of Dopamine Transporter Expression to Incorporate as Part of Overexpression of a Panel of Dopaminergic Genes to Reconstruct a Dopaminergic Cell Line for Therapy in Parkinson's Disease cDNAs for the dopamine transporter, and for tyrosine hydroxylase and aromatic amino acid decarboxylase (DOPA decarboxylase) are transfected into cell types including COS cells as described above. Cells are cotransfected with the neomycin resistance marker, selected by growth in G418, and then tested for their ability to synthesize and accumulate dopamine. Individual subclones may be able to take up dopamine, without the ability to synthesize it. However, individual subclones are also likely to integrate several of the plasmids. If the plasmids cannot be introduced serially or together in this direction, serial edition of tyrosine hydroxylase and DOPA decarboxylase to stable cell lines already expressing the dopamine transporter stably should be employed (see above). The ability of cells to incorporate tritiated tyrosine into tritiated dopamine is tested via HPLC analysis and radiochemical detection as described (Uhl et al., Molecular Brain Research, 1991), their ability to take up tritiated dopamine is performed as described in the same reference.

These same procedures are used in transfecting cells obtained from an individual with Parkinson's disease, so that stable immortalized cell lines expressing dopamine could be constructed with immunologic identity to the patient. Means of controlling the replication of these cells by encapsulating them in a matrix that is not porous to cell bodies, but able to be permeated by cell processes, or by use of inhibitory growth factors, can also be employed. A third strategy, temperature sensitive cell mutants that would not divide under physiologic temperatures (e.g. temperature sensitive COS cells variants) could be used to be able to express the dopaminergic cDNA stably, in a fashion that would produce dopaminergic cells. Each of these cell types are potential candidates for us in transplantation into striatum in individuals with striatal dopamine depletion in Parkinson's disease. Alternatively, genes could be incorporated with retroviral vectors as well-known for practitioners of the art.

EXAMPLE 8

Production of Variant Sequences in DAT1 Protein and Testing of Their Biological Function Site directed mutagenesis using olgonucleotides is used to introduce specific single- and multiple-base changes into the DAT1 cDNA that change specific amino acids in the DAT1 protein. The ability of mutant transporters to take up [$^3$H] dopamine, [$^3$H] MPP+, and to bind [$^3$H] cocaine and cocaine analogues (especially

[³H] CFT) is tested as described above. The Amersham mutagenesis system (version 2.1, technical bulletin code RPN1523) can be used. Initial studies of mutants of the aspartic acid residue in transmembrane domain 1, and the serine residues in transmembrane domain 7 have revealed substantial effects on dopamine transport, and more modest effects on cocaine binding. These results document that the residues key to dopamine transport are not identical to those crucial to cocaine binding; the first transmembrane residue change of aspartic acid (residue 79) to glycine reduces cocaine binding by 10%, but reduces dopamine transport by over 95%. Mutations in the second extracellular domain in glycosylation sites help elucidate the role of glycosylation in the functions of this molecule. Selective removal of the N and C terminal intracellular and second extracellular loop, and production of chimeric molecules with replacement of these regions with the corresponding regions of the GABA transporter further confirm the molecular features of DAT that are essential for dopamine transport and cocaine binding and allow development of agents dissociating the two processes.

EXAMPLE 9

A Biosensor for the Measurement of Dopamine, Cocaine or Analogs thereof in Physiologic Samples Biosensors consisting of DAT1 protein or the ligand binding portions thereof and a piezoelectric crystal can be created and utilized for the measurement of DAT1 ligands in samples. The literature describing the use of ligand binding proteins as components in biosensors is large and expanding. Review of the art is given by Luong, et al. (Luong, J. H. T, et al. Trends Biotehnol. 6, 310-3316 (1988)) and Wingard (Wingrad, L. B. Jr. Ann. N.Y. Acad. Sci 613, 44-53 (1990)), who discusses the applications of neuroreceptors to the art. Specific protocols for the attachment of proteins to piezoelectric crystals made be found in Davis and Leary (Davis, K. A. and Leary, T. R. Anal. Chem 61, 1227-1230 (1989)) Or Guilbault, et al. (Guibault, G. G. et al. Bio/Technology 7, 349-351 (1989)).

EXAMPLE 10

Production of Antibodies to DAT1 and Use of Same in a Diagnostic Test for Dopaminergic Cell Death A. Production of polyclonal antibodies.

DAT1 protein obtained as described above or synthetic polypeptides of amino acid sequence derived from the DAT1 sequence are used as immunogens in an appropriate animal. The serum is obtained from the immunized animal and either utilized directly or the antibody may be purified from the serum by any commonly utilized techniques. Polyclonal antibody directed only toward DAT1 can be isolated by use of an affinity column derivatized with the immunogen utilized to raise the antibody, again using techniques familiar to one knowledgeable in the art.

B. Production of monoclonal antibodies to DAT1

Monoclonal antibodies to DAT1 to particular epitopes of DAT1 may be produced by immunization of an appropriate animal with DAT1 protein obtained as above or with peptides of amino acid sequence derived from the DAT1 amino acid sequence. Hybridoma cultures are then established from spleen cells as described by Jaffe and McMahon-Pratt (Jaffe, C. L. and MacMahon-Pratt, D. J. Immunol. 131, 1987-1993 (1983)). Alternatively, peripheral blood lymphocytes may be isolated and immortalized by transformation with Epstein-Barr virus. These cells produce monoclonal antibodies, but if desired, hybridomas can then be made from the transformed lymphocytes (Yamaguchi, H. et al. Proc. Natl. Acad. Sci. 84, 2416-2420 (1987)). Cell lines producing anti-DAT1 antibodies are identified by commonly employed screening techniques. Monoclonal antibody is then purified by well known techniques from the supernatants of large-scale cultures of the antibody producing cells.

C. Diagnosis of dopaminergic cell death in vivo by immunoassay of cerebrospinal fluid of a patient using anti-DAT1 antibodies.

The death of dopaminergic neurons in the brain of a patient should result in the accumulation in the cerebrospinal fluid, which bathes these cells, of membrane debris as a product of lysis of the dead cells. Other pathologic conditions, short of cell death that result in the release of DAT protein, or degraded peptide fragments of DAT protein into the surrounding medium can also be imagined. The cerebrospinal fluid can be sampled by lumbar puncture of a patient. The presence of degradation products of DAT1 protein is detected by immunoassay, using as the primary antibody at least one of the products obtained as described above. Elevated levels of DAT1 protein detected in the cerebrospinal fluid, compared with the range seen in normal controls is indicative of Parkinson's disease or drug-induced neurotoxicity. Alternatively, disease progression can be monitored by the assessment of DAT1 levels in serial samples from the same patient.

---

We claim:

1. An isolated cDNA comprising a nucleotide sequence which encodes a dopamine transporter protein having the amino acid sequence described in FIG. 3 (SEQ. ID NO: 2) of the specification.

2. An expression plasmid DNA comprising the cDNA of claim 1, a replication DNA sequence that provides for replication of said plasmid in eukaryotic cells, and transcription DNA sequences that provide for transcription of said cDNA in eukaryotic cells, said transcription sequences being operatively linked to said cDNA such that, upon transformation of vertebrate cells not normally displaying dopamine transport activity, a protein is expressed in said cells that confers upon said ells dopamine transport activity and also confers upon said cells the characteristic of binding of 2-beta-carbomethoxy-3-beta-(4-fluorophenyl)tropane (CFT) to membranes of said transformed cells.

3. An expression plasmid DNA as recited in claim 2, wherein the cDNA encodes a protein having a $Kd=46\pm7.8$ nM with number of site values from Scatchard and Hill analyses of 1 for CFT binding.

4. A plasmid DNA comprising the cDNA of claim 1, a replication DNA sequence that provides for replication of said plasmid in a prokaryotic host cell, and transcription DNA sequences that provide for transcription of said cDNA in vitro and that are operatively linked to said cDNA such that the resulting mRNA can be isolated and translated upon introduction into a eukaryotic cell type.

5. An plasmid DNA as recited in claim 4, wherein the cDNA encodes a protein having a $Kd=46\pm7.8$ nM with number of site values from Scatchard and Hill analyses of 1 for CFT binding.

6. A eukaryotic cell line derived from a cell type that does not normally express dopamine transport activity at its surface that has been made to transport dopamine or to bind CFT by the introduction of the DNA of claim 1 into its genome.

7. The cell line of claim 6 where the cell type is COS cells.

8. An isolated cDNA as recited in claim 1, which encodes a protein having a $Kd=46\pm7.8$ nM with number of site values from Scatchard and Hill analyses of 1 for CFT binding.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
      ( A ) LENGTH: 3404 base pairs
      ( B ) TYPE: nucleic acid
      ( C ) STRANDEDNESS: double
      ( D ) TOPOLOGY: linear ( i i ) MOLECULE TYPE: cDNA ( v i ) ORIGINAL SOURCE:
      ( A ) ORGANISM: Rattus rattus ( v i i ) IMMEDIATE SOURCE:
    ( B ) CLONE: pDAT1

( i x ) FEATURE:
    ( A ) NAME/KEY: CDS
    ( B ) LOCATION: 63..1919

( i x ) FEATURE:
    ( A ) NAME/KEY: polyAsite
    ( B ) LOCATION: 3385

( i x ) FEATURE:
    ( A ) NAME/KEY: 5'UTR
    ( B ) LOCATION: 6..62

( i x ) FEATURE:
    ( A ) NAME/KEY: 3'UTR
    ( B ) LOCATION: 1920..3384

( x i ) SEQUENCE DESCRIPTION: SEQ ID NO:1:

```
GAATTCCCGC AGGAGTCAGT CGAAGAAGAA AGAAGCAGAG TTCCTTGGGC TCCGGTCTAC          60

CC ATG AGT AAG AGC AAA TGC TCC GTG GGA CCA ATG TCT TCA GTG GTG           107
   Met Ser Lys Ser Lys Cys Ser Val Gly Pro Met Ser Ser Val Val
   1           5                   10                  15

GCC CCG GCT AAA GAG TCC AAT GCT GTG GGC CCC AGA GAG GTG GAG CTC          155
Ala Pro Ala Lys Glu Ser Asn Ala Val Gly Pro Arg Glu Val Glu Leu
                20                  25                  30

ATC CTG GTC AAG GAG CAG AAC GGA GTG CAG CTG ACC AAC TCC ACC CTC          203
Ile Leu Val Lys Glu Gln Asn Gly Val Gln Leu Thr Asn Ser Thr Leu
            35                  40                  45

ATC AAC CCG CCA CAG ACA CCA GTG GAG GCT CAA GAG CGG GAG ACC TGG          251
Ile Asn Pro Pro Gln Thr Pro Val Glu Ala Gln Glu Arg Glu Thr Trp
        50                  55                  60

AGC AAG AAA ATT GAT TTC CTG CTA TCA GTC ATC GGC TTT GCT GTG GAC          299
Ser Lys Lys Ile Asp Phe Leu Leu Ser Val Ile Gly Phe Ala Val Asp
    65                  70                  75

CTG GCC AAT GTC TGG AGG TTT CCC TAC CTG TGC TAC AAA AAT GGT GGA          347
Leu Ala Asn Val Trp Arg Phe Pro Tyr Leu Cys Tyr Lys Asn Gly Gly
80                  85                  90                  95

GGT GCC TTC CTG GTG CCC TAC CTG CTC TTC ATG GTT ATT GCT GGG ATG          395
Gly Ala Phe Leu Val Pro Tyr Leu Leu Phe Met Val Ile Ala Gly Met
                100                 105                 110

CCC CTC TTC TAC ATG GAG CTG GCT CTC GGA CAG TTC AAC AGA GAA GGA          443
Pro Leu Phe Tyr Met Glu Leu Ala Leu Gly Gln Phe Asn Arg Glu Gly
            115                 120                 125

GCT GGT GGT GTC TGG AAG ATC TGT CCT GTC CTG AAA GGT GTG GGC TTC          491
Ala Gly Gly Val Trp Lys Ile Cys Pro Val Leu Lys Gly Val Gly Phe
        130                 135                 140

ACT GTT ATC CTC ATC TCT TTC TAC GTG GGC TTC TTC TAC AAT GTC ATC          539
Thr Val Ile Leu Ile Ser Phe Tyr Val Gly Phe Phe Tyr Asn Val Ile
145                 150                 155

ATC GCA TGG GCA CTG CAC TAC TTC TTC TCC TCC TTC ACC ATG GAC CTC          587
Ile Ala Trp Ala Leu His Tyr Phe Phe Ser Ser Phe Thr Met Asp Leu
160                 165                 170                 175

CCA TGG ATC CAC TGC AAC AAC ACC TGG AAT AGC CCC AAC TGC TCC GAT          635
Pro Trp Ile His Cys Asn Asn Thr Trp Asn Ser Pro Asn Cys Ser Asp
                180                 185                 190

GCC CAT GCC AGC AAC TCT AGC GAC GGC CTG GGC CTC AAT GAC ACC TTT          683
Ala His Ala Ser Asn Ser Ser Asp Gly Leu Gly Leu Asn Asp Thr Phe
            195                 200                 205

GGG ACC ACA CCC GCT GCT GAG TAC TTT GAG CGT GGC GTG CTG CAC CTT          731
Gly Thr Thr Pro Ala Ala Glu Tyr Phe Glu Arg Gly Val Leu His Leu
        210                 215                 220

CAC CAG AGC CGT GGC ATT GAT GAC CTG GGC CCT CCA CGG TGG CAG CTC          779
His Gln Ser Arg Gly Ile Asp Asp Leu Gly Pro Pro Arg Trp Gln Leu
```

-continued

|     | 225 |     |     |     | 230 |     |     |     | 235 |     |     |     |     |     |     |      |
|-----|-----|-----|-----|-----|-----|-----|-----|-----|-----|-----|-----|-----|-----|-----|-----|------|
| ACA | GCC | TGC | CTG | GTG | CTG | GTC | ATT | GTT | CTG | CTC | TAC | TTC | AGC | CTA | TGG | 827  |
| Thr | Ala | Cys | Leu | Val | Leu | Val | Ile | Val | Leu | Leu | Tyr | Phe | Ser | Leu | Trp |      |
| 240 |     |     |     |     | 245 |     |     |     | 250 |     |     |     |     | 255 |     |      |
| AAG | GGA | GTA | AAG | ACC | TCA | GGG | AAG | GTG | GTG | TGG | ATC | ACA | GCT | ACC | ATG | 875  |
| Lys | Gly | Val | Lys | Thr | Ser | Gly | Lys | Val | Val | Trp | Ile | Thr | Ala | Thr | Met |      |
|     |     |     |     | 260 |     |     |     |     | 265 |     |     |     |     | 270 |     |      |
| CCC | TAT | GTG | GTC | CTC | ACA | GCC | CTG | CTC | CTG | CGT | GGA | GTT | ACC | CTT | CCT | 923  |
| Pro | Tyr | Val | Val | Leu | Thr | Ala | Leu | Leu | Leu | Arg | Gly | Val | Thr | Leu | Pro |      |
|     |     |     |     |     | 275 |     |     |     |     | 280 |     |     |     |     | 285 |      |
| GGA | GCC | ATG | GAT | GGC | ATC | AGA | GCA | TAC | CTC | AGT | GTG | GAC | TTC | TAC | CGA | 971  |
| Gly | Ala | Met | Asp | Gly | Ile | Arg | Ala | Tyr | Leu | Ser | Val | Asp | Phe | Tyr | Arg |      |
|     |     |     | 290 |     |     |     |     | 295 |     |     |     |     | 300 |     |     |      |
| CTC | TGT | GAG | GCA | TCT | GTG | TGG | ATC | GAT | GCT | GCC | ACC | CAG | GTG | TGC | TTC | 1019 |
| Leu | Cys | Glu | Ala | Ser | Val | Trp | Ile | Asp | Ala | Ala | Thr | Gln | Val | Cys | Phe |      |
|     |     | 305 |     |     |     |     | 310 |     |     |     |     | 315 |     |     |     |      |
| TCC | CTC | GGC | GTT | GGG | TTT | GGA | GTG | CTG | ATT | GCC | TTC | TCC | AGT | TAC | AAT | 1067 |
| Ser | Leu | Gly | Val | Gly | Phe | Gly | Val | Leu | Ile | Ala | Phe | Ser | Ser | Tyr | Asn |      |
| 320 |     |     |     |     | 325 |     |     |     |     | 330 |     |     |     |     | 335 |      |
| AAA | TTC | ACC | AAT | AAC | TGC | TAT | AGA | GAC | GCA | ATC | ATC | ACC | ACC | TCC | ATT | 1115 |
| Lys | Phe | Thr | Asn | Asn | Cys | Tyr | Arg | Asp | Ala | Ile | Ile | Thr | Thr | Ser | Ile |      |
|     |     |     |     | 340 |     |     |     |     | 345 |     |     |     |     | 350 |     |      |
| AAC | TCC | CTG | ACA | AGC | TTC | TCC | TCT | GGC | TTC | GTC | GTC | TTC | TCC | TTC | CTG | 1163 |
| Asn | Ser | Leu | Thr | Ser | Phe | Ser | Ser | Gly | Phe | Val | Val | Phe | Ser | Phe | Leu |      |
|     |     |     | 355 |     |     |     |     | 360 |     |     |     |     | 365 |     |     |      |
| GGG | TAT | ATG | GCA | CAG | AAG | CAC | AAT | GTG | CCC | ATC | AGA | GAT | GTG | GCC | ACA | 1211 |
| Gly | Tyr | Met | Ala | Gln | Lys | His | Asn | Val | Pro | Ile | Arg | Asp | Val | Ala | Thr |      |
|     |     | 370 |     |     |     |     | 375 |     |     |     |     | 380 |     |     |     |      |
| GAT | GGA | CCT | GGG | CTC | ATC | TTC | ATC | ATC | TAT | CCT | GAG | GCG | ATC | GCC | ACA | 1259 |
| Asp | Gly | Pro | Gly | Leu | Ile | Phe | Ile | Ile | Tyr | Pro | Glu | Ala | Ile | Ala | Thr |      |
|     | 385 |     |     |     |     | 390 |     |     |     |     | 395 |     |     |     |     |      |
| CTC | CCG | CTG | TCT | TCT | GCC | TGG | GCT | GCT | GTC | TTC | TTC | CTC | ATG | CTG | CTC | 1307 |
| Leu | Pro | Leu | Ser | Ser | Ala | Trp | Ala | Ala | Val | Phe | Phe | Leu | Met | Leu | Leu |      |
| 400 |     |     |     |     | 405 |     |     |     |     | 410 |     |     |     |     | 415 |      |
| ACT | CTG | GGT | ATC | GAC | AGT | GCA | ATG | GGG | GGC | ATG | GAG | TCA | GTG | ATC | ACT | 1355 |
| Thr | Leu | Gly | Ile | Asp | Ser | Ala | Met | Gly | Gly | Met | Glu | Ser | Val | Ile | Thr |      |
|     |     |     |     | 420 |     |     |     |     | 425 |     |     |     |     | 430 |     |      |
| GGG | CTC | GTC | GAT | GAG | TTC | CAG | CTG | CTA | CAT | CGG | CAT | CGA | GAG | CTC | TTC | 1403 |
| Gly | Leu | Val | Asp | Glu | Phe | Gln | Leu | Leu | His | Arg | His | Arg | Glu | Leu | Phe |      |
|     |     |     | 435 |     |     |     |     | 440 |     |     |     |     | 445 |     |     |      |
| ACT | CTT | GGC | ATT | GTC | CTG | GCT | ACT | TTC | CTG | CTG | TCT | CTC | TTC | TGC | GTC | 1451 |
| Thr | Leu | Gly | Ile | Val | Leu | Ala | Thr | Phe | Leu | Leu | Ser | Leu | Phe | Cys | Val |      |
|     |     | 450 |     |     |     |     | 455 |     |     |     |     | 460 |     |     |     |      |
| ACC | AAC | GGT | GGC | ATC | TAC | GTC | TTC | ACA | CTG | CTG | GAC | CAC | TTT | GCA | GCT | 1499 |
| Thr | Asn | Gly | Gly | Ile | Tyr | Val | Phe | Thr | Leu | Leu | Asp | His | Phe | Ala | Ala |      |
| 465 |     |     |     |     | 470 |     |     |     |     | 475 |     |     |     |     |     |      |
| GGC | ACA | TCT | ATC | CTC | TTT | GGC | GTG | CTC | ATT | GAA | GCC | ATT | GGG | GTG | GCC | 1547 |
| Gly | Thr | Ser | Ile | Leu | Phe | Gly | Val | Leu | Ile | Glu | Ala | Ile | Gly | Val | Ala |      |
| 480 |     |     |     |     | 485 |     |     |     |     | 490 |     |     |     |     | 495 |      |
| TGG | TTC | TAC | GGC | GTC | CAG | CAA | TTC | AGT | GAT | GAC | ATC | AAG | CAA | ATG | ACA | 1595 |
| Trp | Phe | Tyr | Gly | Val | Gln | Gln | Phe | Ser | Asp | Asp | Ile | Lys | Gln | Met | Thr |      |
|     |     |     |     | 500 |     |     |     |     | 505 |     |     |     |     | 510 |     |      |
| GGG | CAG | CGA | CCC | AAC | CTG | TAC | TGG | CGG | CTA | TAC | TGG | AAG | CTG | GTC | AGC | 1643 |
| Gly | Gln | Arg | Pro | Asn | Leu | Tyr | Trp | Arg | Leu | Tyr | Trp | Lys | Leu | Val | Ser |      |
|     |     |     | 515 |     |     |     |     | 520 |     |     |     |     | 525 |     |     |      |
| CCC | TGC | TTC | CTC | CTG | TAT | GTG | GTC | GTG | GTC | AGC | ATT | GTG | ACC | TTC | AGA | 1691 |
| Pro | Cys | Phe | Leu | Leu | Tyr | Val | Val | Val | Val | Ser | Ile | Val | Thr | Phe | Arg |      |
|     |     | 530 |     |     |     |     | 535 |     |     |     |     | 540 |     |     |     |      |
| CCC | CCA | CAC | TAT | GGG | GCC | TAC | ATC | TTC | CCA | GAC | TGG | GCC | AAT | GCC | CTG | 1739 |
| Pro | Pro | His | Tyr | Gly | Ala | Tyr | Ile | Phe | Pro | Asp | Trp | Ala | Asn | Ala | Leu |      |
| 545 |     |     |     |     | 550 |     |     |     |     | 555 |     |     |     |     |     |      |

-continued

| | | | | | | | | | | | | | | | | |
|---|---|---|---|---|---|---|---|---|---|---|---|---|---|---|---|---|
| GGC | TGG | ATC | ATC | GCC | ACA | TCC | TCC | ATG | GCC | ATG | GTG | CCC | ATT | TAT | GCG | 1787 |
| Gly | Trp | Ile | Ile | Ala | Thr | Ser | Ser | Met | Ala | Met | Val | Pro | Ile | Tyr | Ala | |
| 560 | | | | | 565 | | | | 570 | | | | | | 575 | |
| ACC | TAC | AAG | TTC | TGC | AGC | CTG | CCG | GGG | TCC | TTC | CGG | GAG | AAA | CTG | GCC | 1835 |
| Thr | Tyr | Lys | Phe | Cys | Ser | Leu | Pro | Gly | Ser | Phe | Arg | Glu | Lys | Leu | Ala | |
| | | | | 580 | | | | | 585 | | | | | 590 | | |
| TAT | GCC | ATC | ACA | CCT | GAG | AAA | GAC | CAT | CAG | CTA | GTG | GAC | AGA | GGG | GAG | 1883 |
| Tyr | Ala | Ile | Thr | Pro | Glu | Lys | Asp | His | Gln | Leu | Val | Asp | Arg | Gly | Glu | |
| | | | 595 | | | | | 600 | | | | | 605 | | | |
| GTG | CGC | CAA | TTC | ACG | CTG | CGT | CAC | TGG | CTG | TTG | CTG | TAAAGTGGAA | | | | 1929 |
| Val | Arg | Gln | Phe | Thr | Leu | Arg | His | Trp | Leu | Leu | Leu | | | | | |
| | | 610 | | | | | 615 | | | | | | | | | |

| | | | | | |
|---|---|---|---|---|---|
| GGAGACAGCT | GCCAGCTGGG | CCACCTCACA | ACAGCGGGGA | CAGGGAGATC | GCAAAGGAAA | 1989 |
| CCCACGAGTC | AAGAAAGGAA | GGAGGGCCAC | TTCCATGCTT | CTCCTTTGTC | GTACGGAAAA | 2049 |
| ATAATCGAAG | CATGGGCTTC | AACCTTTGAC | TGTTCACACC | CAAATCATTG | CCACAAAGAA | 2109 |
| GCCTCTGTCT | GTGTATGGCT | GTAAAACAT | ACACCTCTAC | ACAGTGAGGT | CAACAATGTC | 2169 |
| CCTGTCCCTA | CTGGGTGGGA | AAACCCTAGC | TGGTATCCTG | TCCCTGCAAG | GCTGACTCCC | 2229 |
| CCATCTGTGG | TCACTCTGGG | AGAACAGGTC | ATACTGCCCC | CTGAATTCTA | GAAGGACCTT | 2289 |
| GGTACCTGTA | CATACACTGT | GCCAGAATCC | TTGTGCTCAC | AGTAGTTGCC | TAAACCAATT | 2349 |
| CTGTTGCTTA | CATTTACAGT | GTCAAGTATC | CTATTTTGCT | GTTGGTAGAA | AAGACAGTTA | 2409 |
| ATACATGCCA | AGTCCTTTCC | TGGTGCTTGG | CTCCGAGCAG | ACACCTTAGC | ATTCTGTTCA | 2469 |
| CACATTACAC | ACACACACAC | ACACACACAC | ACACACACAC | ACACACACAC | ACACACGGTC | 2529 |
| TGTTCTGAGC | CACGGAGGAC | AAGGGACTTG | GTGCAAGTGA | CCAGAGATTA | TGTTTTTCCT | 2589 |
| TTATAGATGA | GATAAATAAA | ATTCGTGAAA | TAAGGTTGGG | AGACACACCC | TACCCCTGGC | 2649 |
| CCCTGGAAGG | CCTGGTCAGC | TTGCAGCCAC | TTTAGTATGG | ACTTGTAGGC | CACATAAAAA | 2709 |
| GTGTACTCTT | CATAGTCAGT | GTGTCCTCAC | CTTCTGGACA | CCTGCTCTGC | ACAGGGTCTC | 2769 |
| GAGATAACTT | GAAGACCATA | TTCTTGGCCT | AGAGCCCTAC | CTGGTCTTCA | AGGAAAGACA | 2829 |
| CCCACTGTAG | GGTTTGATTT | CCTACTGGCT | CCTGTCACAT | CAATGGACAT | TATCCATGTT | 2889 |
| ATAAATGACT | TTTTAAAACC | ATATTTATGT | GTGAATCGAA | CTTACTCTCA | AAATGCAAGG | 2949 |
| TTAGTTTGTT | CAAATCCATT | TGCTGAAGAG | TAATTAGTGT | AAGAGGAAGG | TATGCCAAGA | 3009 |
| ATCACCTTCT | TCCCGGAGCA | CTGGCTTTAG | TTCCTGGAGT | GAAAAGTGGA | TGTCATGATT | 3069 |
| TTCCTTGAGC | TAATAAATGC | AAACTTTGGC | CTGGCCTGTG | TCCTATATAA | GTGGCACCAT | 3129 |
| GTGTCTCCCT | GAGAGAGAGT | CAACCTTAGT | ATTCTCTGCA | AGTATACATT | GGCACGAGGG | 3189 |
| TGTTAAATGT | GCTACCAGGG | TGTTAAATGC | AGGCCTGTTG | GCTTTGAGAC | TGTAGTATGG | 3249 |
| CAGAGAAGGC | TCCGGTTTAC | CATCTCTCAG | AGGAGTGGCT | CCATGTAGAC | ATCCAGGTGT | 3309 |
| TGTAAGCATC | TGTTTTTTGT | GTCTATAGCC | AGTACCTTGT | GTGGGTTCTT | ACAAACAATA | 3369 |
| AAGAAATAT | ATGTTGGAAA | AAAAAAAGG | AATTC | | | 3404 |

( 2 ) INFORMATION FOR SEQ ID NO:2:

( i ) SEQUENCE CHARACTERISTICS:
        ( A ) LENGTH: 619 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ser | Lys | Ser | Lys | Cys | Ser | Val | Gly | Pro | Met | Ser | Ser | Val | Val | Ala |
| 1 | | | | 5 | | | | | 10 | | | | | 15 | |
| Pro | Ala | Lys | Glu | Ser | Asn | Ala | Val | Gly | Pro | Arg | Glu | Val | Glu | Leu | Ile |

```
                    20                          25                              30

Leu  Val  Lys  Glu  Gln  Asn  Gly  Val  Gln  Leu  Thr  Asn  Ser  Thr  Leu  Ile
          35                       40                      45

Asn  Pro  Pro  Gln  Thr  Pro  Val  Glu  Ala  Gln  Glu  Arg  Glu  Thr  Trp  Ser
     50                       55                      60

Lys  Lys  Ile  Asp  Phe  Leu  Leu  Ser  Val  Ile  Gly  Phe  Ala  Val  Asp  Leu
65                       70                      75                           80

Ala  Asn  Val  Trp  Arg  Phe  Pro  Tyr  Leu  Cys  Tyr  Lys  Asn  Gly  Gly  Gly
                    85                       90                      95

Ala  Phe  Leu  Val  Pro  Tyr  Leu  Leu  Phe  Met  Val  Ile  Ala  Gly  Met  Pro
               100                      105                     110

Leu  Phe  Tyr  Met  Glu  Leu  Ala  Leu  Gly  Gln  Phe  Asn  Arg  Glu  Gly  Ala
               115                      120                     125

Gly  Gly  Val  Trp  Lys  Ile  Cys  Pro  Val  Leu  Lys  Gly  Val  Gly  Phe  Thr
     130                      135                     140

Val  Ile  Leu  Ile  Ser  Phe  Tyr  Val  Gly  Phe  Phe  Tyr  Asn  Val  Ile  Ile
145                      150                     155                          160

Ala  Trp  Ala  Leu  His  Tyr  Phe  Phe  Ser  Ser  Phe  Thr  Met  Asp  Leu  Pro
               165                      170                     175

Trp  Ile  His  Cys  Asn  Asn  Thr  Trp  Asn  Ser  Pro  Asn  Cys  Ser  Asp  Ala
               180                      185                     190

His  Ala  Ser  Asn  Ser  Ser  Asp  Gly  Leu  Gly  Leu  Asn  Asp  Thr  Phe  Gly
          195                      200                     205

Thr  Thr  Pro  Ala  Ala  Glu  Tyr  Phe  Glu  Arg  Gly  Val  Leu  His  Leu  His
     210                      215                     220

Gln  Ser  Arg  Gly  Ile  Asp  Asp  Leu  Gly  Pro  Pro  Arg  Trp  Gln  Leu  Thr
225                      230                     235                          240

Ala  Cys  Leu  Val  Leu  Val  Ile  Val  Leu  Leu  Tyr  Phe  Ser  Leu  Trp  Lys
               245                      250                     255

Gly  Val  Lys  Thr  Ser  Gly  Lys  Val  Val  Trp  Ile  Thr  Ala  Thr  Met  Pro
               260                      265                     270

Tyr  Val  Val  Leu  Thr  Ala  Leu  Leu  Leu  Arg  Gly  Val  Thr  Leu  Pro  Gly
          275                      280                     285

Ala  Met  Asp  Gly  Ile  Arg  Ala  Tyr  Leu  Ser  Val  Asp  Phe  Tyr  Arg  Leu
     290                      295                     300

Cys  Glu  Ala  Ser  Val  Trp  Ile  Asp  Ala  Ala  Thr  Gln  Val  Cys  Phe  Ser
305                      310                     315                          320

Leu  Gly  Val  Gly  Phe  Gly  Val  Leu  Ile  Ala  Phe  Ser  Ser  Tyr  Asn  Lys
                    325                      330                     335

Phe  Thr  Asn  Asn  Cys  Tyr  Arg  Asp  Ala  Ile  Ile  Thr  Thr  Ser  Ile  Asn
               340                      345                     350

Ser  Leu  Thr  Ser  Phe  Ser  Ser  Gly  Phe  Val  Val  Phe  Ser  Phe  Leu  Gly
          355                      360                     365

Tyr  Met  Ala  Gln  Lys  His  Asn  Val  Pro  Ile  Arg  Asp  Val  Ala  Thr  Asp
     370                      375                     380

Gly  Pro  Gly  Leu  Ile  Phe  Ile  Ile  Tyr  Pro  Glu  Ala  Ile  Ala  Thr  Leu
385                      390                     395                          400

Pro  Leu  Ser  Ser  Ala  Trp  Ala  Ala  Val  Phe  Phe  Leu  Met  Leu  Leu  Thr
               405                      410                     415

Leu  Gly  Ile  Asp  Ser  Ala  Met  Gly  Gly  Met  Glu  Ser  Val  Ile  Thr  Gly
               420                      425                     430

Leu  Val  Asp  Glu  Phe  Gln  Leu  Leu  His  Arg  His  Arg  Glu  Leu  Phe  Thr
          435                      440                     445

Leu  Gly  Ile  Val  Leu  Ala  Thr  Phe  Leu  Leu  Ser  Leu  Phe  Cys  Val  Thr
          450                      455                     460
```

| | | | | | | | | | | | | | | |
|---|---|---|---|---|---|---|---|---|---|---|---|---|---|---|
| Asn 465 | Gly | Gly | Ile | Tyr | Val 470 | Phe | Thr | Leu | Leu | Asp 475 | His | Phe | Ala | Ala Gly 480 |
| Thr | Ser | Ile | Leu | Phe 485 | Gly | Val | Leu | Ile | Glu 490 | Ala | Ile | Gly | Val | Ala Trp 495 |
| Phe | Tyr | Gly | Val 500 | Gln | Gln | Phe | Ser | Asp 505 | Asp | Ile | Lys | Gln | Met 510 | Thr Gly |
| Gln | Arg | Pro 515 | Asn | Leu | Tyr | Trp | Arg 520 | Leu | Tyr | Trp | Lys | Leu 525 | Val | Ser Pro |
| Cys | Phe 530 | Leu | Leu | Tyr | Val | Val 535 | Val | Val | Ser | Ile | Val 540 | Thr | Phe | Arg Pro |
| Pro 545 | His | Tyr | Gly | Ala | Tyr 550 | Ile | Phe | Pro | Asp | Trp 555 | Ala | Asn | Ala | Leu Gly 560 |
| Trp | Ile | Ile | Ala | Thr 565 | Ser | Ser | Met | Ala | Met 570 | Val | Pro | Ile | Tyr | Ala Thr 575 |
| Tyr | Lys | Phe | Cys 580 | Ser | Leu | Pro | Gly | Ser 585 | Phe | Arg | Glu | Lys | Leu 590 | Ala Tyr |
| Ala | Ile | Thr 595 | Pro | Glu | Lys | Asp | His 600 | Gln | Leu | Val | Asp | Arg 605 | Gly | Glu Val |
| Arg | Gln | Phe 610 | Thr | Leu | Arg | His 615 | Trp | Leu | Leu | Leu | | | | |

(2) INFORMATION FOR SEQ ID NO:3:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (iv) ANTI-SENSE: YES (ix) FEATURE:
        (A) NAME/KEY: -
        (B) LOCATION: 1..35
        (D) OTHER INFORMATION: /label=oligo
            / note="synthetic oligonucleotide utilized in
            localization of DAT1 mRNA expression in brain by
            in situ hybridization"

(xi) SEQUENCE DESCRIPTION: SEQ ID NO:3:

TAAAGCCAGT GCTCCGGGAG GAGGGTGATT CTTGG      35

(2) INFORMATION FOR SEQ ID NO:4:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (iv) ANTI-SENSE: NO (ix) FEATURE:
        (A) NAME/KEY: -
        (B) LOCATION: 1..62
        (D) OTHER INFORMATION: /label=oligo
            / note="degenerate synthetic oligo used to screen
            library for DAT1 transporter candidate clones
            based on homology to GABA and norepinephrine
            transporters."

( x i ) SEQUENCE DESCRIPTION: SEQ ID NO:4:

TAGGGGATCA GGAAGRCACC TCCGCCGTTC TTGTAGCACA GGTAGGGGAA GCGCCACACG    60

TT    62

( 2 ) INFORMATION FOR SEQ ID NO:5:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( i x ) FEATURE:
        ( A ) NAME/KEY: -
        ( B ) LOCATION: 1..31
        ( D ) OTHER INFORMATION: /label=oligonucleotide
            / note="Upstream primer for generation of PCR
            product used as probe to screen library for clones
            homologous to GABA and norepinephrine
            transporters."

( i x ) FEATURE:
        ( A ) NAME/KEY: modifiedbase
        ( B ) LOCATION: 14
        ( D ) OTHER INFORMATION: /modbase=i ( i x ) FEATURE:
        ( A ) NAME/KEY: modifiedbase
        ( B ) LOCATION: 20
        ( D ) OTHER INFORMATION: /modbase=i ( i x ) FEATURE:
        ( A ) NAME/KEY: modifiedbase
        ( B ) LOCATION: 26
        ( D ) OTHER INFORMATION: /modbase=i ( x i ) SEQUENCE DESCRIPTION: SEQ ID NO:5:

CGGGATCCAA YGTNTGGMGN TTYCCNTAYY T    31

( 2 ) INFORMATION FOR SEQ ID NO:6:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: YES ( i x ) FEATURE:
        ( A ) NAME/KEY: -
        ( B ) LOCATION: 1..33
        ( D ) OTHER INFORMATION: /label=oligonucleotide
            / note="downstream primer for PCR generation of
            probe for screening of library to detect clones
            homologous to GABA and norepinephrine
            transporters."

( i x ) FEATURE:
        ( A ) NAME/KEY: modifiedbase
        ( B ) LOCATION: 19
        ( D ) OTHER INFORMATION: /modbase=i ( x i ) SEQUENCE DESCRIPTION: SEQ ID NO:6:

GCGAATTCCC AGGCCRTANS WRAARAARAT YTG    33